US010928396B2

(12) United States Patent
Shaw et al.

(10) Patent No.: US 10,928,396 B2
(45) Date of Patent: Feb. 23, 2021

(54) BIN1 EXPRESSION AS A MARKER OF CANCER

(71) Applicant: Sarcotein Diagnostics, LLC, Tampa, FL (US)

(72) Inventors: Darryl Steven Shaw, Tampa, FL (US); Neil Gavin Shaw, Tampa, FL (US)

(73) Assignee: SARCOTEIN DIAGNOSTICS, LLC, Tampa, FL (US)

( * ) Notice: Subject to any disclaimer, the term of this patent is extended or adjusted under 35 U.S.C. 154(b) by 374 days.

(21) Appl. No.: 15/827,568

(22) Filed: Nov. 30, 2017

(65) Prior Publication Data

US 2018/0172693 A1 Jun. 21, 2018

Related U.S. Application Data

(63) Continuation of application No. 14/348,269, filed as application No. PCT/US2012/058051 on Sep. 28, 2012, now Pat. No. 9,846,159.

(60) Provisional application No. 61/541,539, filed on Sep. 30, 2011.

(51) Int. Cl.
| C07K 16/00 | (2006.01) |
| G01N 33/574 | (2006.01) |
| C07K 16/18 | (2006.01) |
| C07K 16/30 | (2006.01) |
| C07K 14/47 | (2006.01) |
| A61K 31/405 | (2006.01) |
| A61K 31/4245 | (2006.01) |
| A61K 39/00 | (2006.01) |

(52) U.S. Cl.
CPC ..... *G01N 33/57488* (2013.01); *A61K 31/405* (2013.01); *A61K 31/4245* (2013.01); *C07K 14/47* (2013.01); *C07K 16/18* (2013.01); *C07K 16/30* (2013.01); *G01N 33/57407* (2013.01); *G01N 33/57419* (2013.01); *G01N 33/57423* (2013.01); *G01N 33/57438* (2013.01); *G01N 33/57449* (2013.01); *G01N 33/57496* (2013.01); *A61K 2039/505* (2013.01); *G01N 2333/4704* (2013.01); *G01N 2800/50* (2013.01); *G01N 2800/52* (2013.01)

(58) Field of Classification Search
CPC ............ G01N 33/57488; A61K 31/405; A61K 31/4245
See application file for complete search history.

(56) References Cited

U.S. PATENT DOCUMENTS

| 4,342,566 A | 8/1982 | Theofilopoulos et al. |
| 6,048,702 A | 4/2000 | Prendergast et al. |
| 6,410,237 B1 | 6/2002 | Brewer et al. |
| 6,410,238 B1 | 6/2002 | Prendergast et al. |
| 6,461,828 B1 | 10/2002 | Stanton et al. |
| 6,831,063 B1 | 12/2004 | Prendergast et al. |
| 7,150,968 B2 | 12/2006 | Prendergast et al. |
| RE39,816 E | 9/2007 | Stanton et al. |
| 8,999,659 B2 | 4/2015 | Shaw et al. |
| 9,150,924 B2 | 10/2015 | Shaw et al. |
| 9,846,159 B2 | 12/2017 | Shaw et al. |
| 9,891,232 B2 | 2/2018 | Shaw et al. |
| 2003/0166021 A1 | 9/2003 | Prendergast et al. |
| 2004/0106954 A1 | 6/2004 | Whitehurst et al. |
| 2004/0241764 A1 | 12/2004 | Galili |
| 2005/0064455 A1 | 3/2005 | Baker et al. |
| 2005/0260697 A1 | 11/2005 | Wang et al. |
| 2006/0003959 A1 | 1/2006 | Burden et al. |
| 2006/0263813 A1 | 11/2006 | Rosenberg et al. |
| 2009/0088482 A1 | 4/2009 | Maybaum et al. |
| 2010/0086481 A1 | 4/2010 | Baird et al. |
| 2010/0092983 A1 | 4/2010 | Liew |
| 2011/0008346 A1 | 1/2011 | Duckers |
| 2011/0217713 A1 | 9/2011 | Weaver et al. |
| 2012/0094300 A1 | 4/2012 | Shaw et al. |
| 2013/0266975 A1 | 10/2013 | Shaw et al. |
| 2013/0324432 A1 | 12/2013 | Shaw et al. |
| 2015/0233947 A1 | 8/2015 | Shaw et al. |
| 2018/0038874 A1 | 2/2018 | Shaw et al. |

FOREIGN PATENT DOCUMENTS

| WO | WO-94/29348 | 12/1994 |
| WO | WO-98/55151 A1 | 12/1998 |
| WO | WO-01/04354 A2 | 1/2001 |
| WO | WO-2007/130549 | 11/2007 |

(Continued)

OTHER PUBLICATIONS

Casset et al., "A peptide mimetic of an anti-CD4 monoclonal antibody by rational design", Biochemical and Biophysical Research Communications, 2003, vol. 307, pp. 198-205.

(Continued)

*Primary Examiner* — Mark Halvorson

(74) *Attorney, Agent, or Firm* — Foley & Lardner LLP

(57) ABSTRACT

Provided are methods for screening a subject for cancer. The methods involve obtaining a blood sample from the subject and determining a level of Bridging Integrator 1 (BIN1) isoforms comprising exon 12a in the sample. Optionally, the method involves determining a level of 12a+/13− BIN isoform (comprising exon 12a but lacking exon 13) in the sample. An elevated level of 12a+(e.g., 12a+/13−) BIN1 isoforms in the blood sample indicates the subject has cancer. Also provided are methods for determining efficacy of a cancer therapy in a subject and methods of treating cancer. Isolated antibodies that selectively bind human 12a+ BIN1 are also provided as well as kits for determining 12a+/13− BIN1 isoforms.

13 Claims, 11 Drawing Sheets

Specification includes a Sequence Listing.

(56) References Cited

FOREIGN PATENT DOCUMENTS

| WO | WO-2010/124240 A2 | 10/2010 |
|---|---|---|
| WO | WO-2012/054764 A1 | 4/2012 |
| WO | WO-2012/087437 | 6/2012 |
| WO | WO-2013/049666 A1 | 4/2013 |

OTHER PUBLICATIONS

Ge et al., "Mechanism for elimination of a tumor suppressor: Aberrant splicing of a brain-specific exon causes loss of function of Bin1 in melanoma," Proc. Natl. Acad. Sci. USA, Aug. 1999, 96(17): 9689-9694.
Holm et al., "Functional mapping and single chain construction of the anti-cytokeratin 8 monoclonal antibody TS1", Molecular Immunology, 2007, vol. 44, pp. 1075-1084.
Hong et al., "Plasma BIN1 correlates with heart failure and predicts arrhythmia in patients with arrhythmogenic right ventricular cardiomyopathy," Heart Rhythm, Jun. 2012, 9(6): 961-7.
Karni et al., "The gene encoding the splicing factor SF2/ASF is a proto-oncogene," Nature Structural & Molecular Biology, vol. 14, No. 3, Mar. 2007, pp. 185-193.
Lonberg et al., "Human Antibodies from Transgenic Mice," Intern. Rev. Immunol., vol. 13, 1995, pp. 65-93.
MacCallum et al., "Antibody-antigen Interactions: Contact Analysis and Binding Site Topography", J. Mol. Biol., 262:732-745, Oct. 1996.
Muller et al., "Inhibition of indoleamine 2,3-dioxygenase, an immunoregulatory target of the cancer suppression gene Bin1, potentiates cancer chemotherapy," Nature Medicine, Mar. 2005, 11(3): 312-319.
Muller, "Marrying Immunotherapy with Chemotherapy: Why Say IDO", Cancer Research, vol. 65, No. 18, (Sep. 15, 2005), pp. 8065-868.
Novitskiy et al., "Turn Off the IDO: Will Clinical Trials Be Successful?," Cancer Discovery, Aug. 2012, 2(8): 673-675.
Pascalis et al., "Grafting of "Abbreviated" complementarity-determining regions containing specificity-determining residues essential for ligand contact to engineer a less immunogenic humanized monoclonal antibody", Journal of Immunology, 2002, vol. 169, pp. 3076-3084.
Paul, "Fundamental Immunology", 3rd Edition, 1993, pp. 292-295.
PCT International Preliminary Report on Patentability (Chapter 1) for Application No. PCT/US2012/058051 dated Apr. 1, 2014. (10 pages).
PCT International Search Report and Written Opinion for Application No. PCT/US2012/058051 dated Jan. 28, 2013. (18 pages).
Pineda-Lucena et al., "A Structure-based Model of the c-Myc/Bin1 Protein Interaction Shows Alternative Splicing of Bin1 and c-Myc Phosphorylation are Key Binding Determinants," J. Mol. Biol. (2005) 351, pp. 182-194.
Prendergast et al., "BAR the door: cancer suppression by amphiphysin-like genes," Biochim Biophys Acta., Jan. 2009, 1795(1): 25-36.
Radpour et al., "Hypermethylation of Tumor Suppressor Genes Involved in Critical Regulatory Pathways for Developing a Blood-Based Test in Breast Cancer," PLoS One 6(1): e16080, Jan. 2011, 11 pages.
Roy et al., "Evidence that public database records for many cancer-associated genes reflect a splice form found in tumors and lack normal splice forms", Nucl Acid Res, 2005; 33:5026-5032.
Rudikoff et al., "Single amino acid substitution altering antigen-binding specificity", Proc. Natl. Acad. Sci. USA, 79(6):1979-1983, Mar. 1982.
Schneider, "Tumor markers in detection of lung cancer", Adv Clin Chem, 2006; 42:1-41.
Smith et al., "IDO Is a Nodal Pathogenic Driver of Lung Cancer and Metastasis Development," Cancer Discovery, Aug. 2012, 2(8): 722-735.

Tajiri et al., "Expression of a MYCN-interacting Isoform of the Tumor Suppressor BIN1 is Reduced in Neuroblastomas with Unfavorable Biological Features", Clinical Cancer Research, (Sep. 5, 2013), pp. 3345-3355.
Thomas et al., "Serum tumor markers: past, state of the art, and future", Int J Biol Markers, 2001; 16:73-86.
Tockman et al., "Considerations in bringing a cancer biomarker to clienical application", Cancer Res., 1992, 52:2711s-2718s.
Wechsler-Reya et al., "Structural Analysis of the Human BIN1 Gene. Evidence for Tissue-Specific Transcriptional Regulation and Alternate RNA Splicing", The Journal of Biological Chemistry, 1997, 272(50):31453-31458.
Xu et al., "Discovery of novel splice forms and functional analysis of cancer-specific alternative splicing in human expressed sequences," Nucleic Acids Research, Oct. 2003, 31(19): 5635-5643.
Edwards et al., "The Remarkable Flexibility of the Human Antibody Repertoire; Isolation of Over One Thousand Different Antibodies to a Single Protein, BLyS," Journal of Mol. Biol., vol. 334, pp. 103-118, 2003.
Lamminmaki et al., "Crystal Structure of a Recombinant Anti-estrafiol Fab Fragment in Complex with 17ß-Estradiol," The Journal of Biological Chemistry, vol. 276, No. 39, pp. 36687-36694, 2001.
Lloyd et al, "Modelling the human immune response: performance of 10 human antibody repertoire against a broad panel of therapeutically relevant antigens," Protein Engineering, Design & Selection, vol. 22 No. 3, pp. 159-168, 2009.
Non-Final Office Action on U.S. Appl. No. 15/555,043 dated Dec. 4, 2018.
Padlan et al., "Structure of an antibody-antigen complex: Crystal structure of the HyHEL-10 Fab-lysozyme complex," Proc. Natl. Acad. Sci. vol. 86, pp. 5938-5942, 1989.
Ward et al., "Binding activities of a repertoire of single immunoglobulin variable domains secreted from *Escherichia coli*," Letters to Nature, vol. 341 Issue 6242, pp. 544-546 pages, 1989.
*Ariosa Diagnostics, Inc. v. Sequenom, Inc.*, Opinion of the US Court of Appeals for the Federal Circuit, 2015, 1-21.
Barth, et al. (2002) "Dissecting interactions between EBI, microtubules and APC in cortical clusters at the plasma membrane", J. Cell Sci., 115(Pt. 8): 1583-1590.
Basso et al., "Arrhythmogenic right ventricular cardiomyopathy", The Lancet, vol. 373, Issue 9671, Apr. 11-17, 2009, pp. 1289-1300.
Bers (2002) "Cardiac excitation-contraction coupling", Nature 415(6868): 198-205.
Beuckelmann et al., "Intracellular calcium handling in isolated ventricular myocytes from patients with terminal heart failure", Circulation, Mar. 1992; 85(3):1046-55.
Birks et al., "Left ventricular assist device and drug therapy for the reversal of heart failure", N Engl J Med., 2006, 355(18):1873-84.
Blaxall et al., "Differential gene expression and genomic patient stratification following left ventricular assist device support", J Am Coll Cardiol., Apr. 2, 2003;41(7):1096-1106.
Bodor et al. (1997) "Troponin I Phosphorylation in the Normal and Failing Adult Human Heart" Circulation 96(5):1495-1500.
Brette & Orchard (2007) "Resurgence of Cardiac T-Tubule Research" Physiology (Bethesda) 22:167-173.
Butler, et al. (1997) "Amphiphysin II (SH3P9; BIN1), a member of the amphiphysin/Rvs family, is concentrated in the cortical cytomatrix of axon initial segments and nodes of ranvier in brain and around T tubules in skeletal muscle", J. Cell Biol. 137(6):1355-1367.
Chang et al., "BIN1 (bridging integrator 1)," Atlas Genet Cytogenet Oncol Haematol., (2009), 13(8):543-548.
Chang, et al. (2007) Bin1 Ablation in Mammary Gland Delays Tissue Remodeling and Drives Cancer Progression. Cancer Res. 67(1):100-107.
Chang, et al. (2007) Bin1 Ablation Increases Susceptibility to Cancer during Aging, Particularly Lung Cancer. Cancer Res. 67(16):7605-7612.
Chen, et al. (2002) "L-type Ca2+ channel density and regulation are altered in failing human ventricular myocytes and recover after support with mechanical assist devices" Circ. Res. 91(6):517-524.
Cheng, et al. (1993) "Calcium sparks: elementary events underlying excitation-contraction coupling in heart muscle" Science 262(5134):740-744.

(56) References Cited

OTHER PUBLICATIONS

Dalzell et al., "Novel biomarkers in heart failure: An overview", Biomarkers in Medicine, Future Medicine, London, (2009), vol. 3, No. 5, pp. 453-463.
De Groote et al., "The impact of beta-adrenoreceptor genepolymorphisms on survival in patients with congestive heart failure", Eur J Heart Fail, (2005), vol. 7, No. 6, p. 966-973.
Dipla, et al. (1998) "Myocyte recovery after mechanical circulatory support in humans with end-stage heart failure" Circulation 97 :2316-2322.
Doust et al., "How well does B-type natriuretic peptide predict death and cardiac events in patients with heart failure: systematic review", BMJ, 2005, 330(7492):625. Review.
Etienne-Manneville & Hall (2003) "Cdc42 regulates GSK-3~ and adenomatous polyposis coli to control cell polarity" Nature 421(6924):753-756.
Fabiato (1983) "Calcium-induced release of calcium from the cardiac sarcoplasmic reticulum" Am. J. Physiol. 245(I):CI-C14.
Fernando et al., "Bin 1 Src Homology 3 Domain Acts as a Scaffold for Myofiber Sarcomere Assembly," J. of Biological Chemistry, (2009), 284(40):27674-27686.
Gomez, et al. (1997) "Defective excitation-contraction coupling in experimental cardiac hypertrophy and heart failure" Science 276(5313):800-806.
Green, et al. (2005) "APC and EBI function together in mitosis to regulate spindle dynamics and chromosome alignment" Mal. Biol. Cell 16(10):4609-4622.
Gwathmey, et al. (1987) "Abnormal intracellular calcium handling in myocardium from patients with end-stage heart failure" Circ. Res. 61(1):70-76.
Hama et al. (1995) "Rapid Ventricular Induction of Brain Natriuretic Peptide Gene Expression in Experimental Acute Myocardial Infarction" Circulation 92(6):1558-1564.
Harding, et al. (1994) "Contractile function and response to agonists in myocytes from failing human heart" Eur. Heart J. 15(Suppl. D):35-36.
Hasenfuss, et al. (1999) "Relationship between Na+-Ca2+-exchanger protein levels and diastolic function of failing human myocardium" Circulation 99(5):641-648.
Hasenfuss, G., "Alterations of calcium-regulatory proteins in heart failure", Cardiovasc Res., 1998, 37(2):279-89. Review.
Hesse et al., "Dilated cardiomyopathy is associated with reduced expression of the cardiac sodium channel Scn5a", Cardiovasc Res., (2007), vol. 75, No. 3, p. 498-509.
Hong et al., "BIN1 localizes the L-type calcium channel to cardiac T-tubules", PLoS Biol., (Feb. 16, 2010), vol. 8, No. 2, pp. E1000312-1-E1000312-14.
Hong et al., "Cardiac BIN1 Folds T-tubule Membrane, Controlling Ion Flux and Limiting Arrhythmia," Nature Medicine, (2014), vol. 20(6):624-632.
Horwitz et al., "Detection of cardiac allograft rejection and response to immunosuppressive therapy with peripheral blood gene expression", Circulation, 2004, 110(25):3815-21.
Huang et al. (1999) "Cardiac troponin I gene knockout: a mouse model of myocardial troponin I deficiency" Circ Res 84(1):1-8.
Hullin, et al. (1999) "Subunit expression of the cardiac L-type calcium channel is differentially regulated in diastolic heart failure of the cardiac allograft" Circulation 100(2):155-163.
Hulot et al. (2004) "Natural history and risk stratification of arrhythmogenic right ventricular dysplasia/cardiomyopathy" Circulation 110(14): 1879-1884.
Hunkeler et al. (1991) "Troponin I isoform expression in human heart" Circ Res 69(5):1409-1414.
Inui, et al. (1987) "Isolation of the ryanodine receptor from cardiac sarcoplasmic reticulum and identity with the feet structures" J. Biol. Chem. 262(32):15637-15642.
Labaer et al., "So, You Want to Look for Biomarkers (Introduction to the Special Biomarkers Issue", Journal of Proteome Research, 2005, vol. 4(4), pp. 1053-1059.
Lee et al., "Amphiphysin 2 (Bin1) and T-tubule biogenesis in muscle", Science, (2002) 297: 1193-1196.
Lehn Art, et al. (2005) "Phosphodiesterase 4D deficiency in the ryanodine-receptor complex promotes heart failure and arrhythmias" Cell 123(1):25-35.
Ligon & Holzbaur (2007) "Microtubules tethered at epithelial cell junctions by dynein facilitate efficient junction assembly" Traffic 8(7):808-819.
LIMR Link the Newsletter of the Lankenau Institute for Medical Research, Summer 2008. www.lirnr.org.
Litwin, et al. (2000) "Dyssynchronous Ca(2+) sparks in myocytes from infarcted hearts" Circ. Res. 87(11):1040-1047.
Lukaski, H., "Sarcopenia: Assessment of Muscle Mass", American Society for Nutritional Sciences, 1997, 127:994S-997S.
Maeda et al., "High levels of plasma brain natriuretic peptide and interleukin-6 after optimized treatment for heart failure are independent risk factors for morbidity and mortality in patients with congestive heart failure", J Am Coll Cardiol., 2000, 36(5):1587-1593.
Marcus et al. (2010) "Diagnosis of arrhythmogenic right ventricular cardiomyopathy/dysplasia: proposed modification of the task force criteria" Circulation 121:1533-1541.
Marx, et al. (2000) "PKA phosphorylation dissociates FKBP12.6 from the calcium release channel (ryanodine receptor): defective regulation in failing hearts" Cell 101(4):365-376.
Mayeux et al., "Biomarkers: Potential uses and Limitations", NeuroRx, 2004, vol. 1, pp. 182-188.
McKenna, Circulation, 1996; 93: 841-842, Report of the 1995 World Health Organization/International Society and Federation of Cardiology Task Force on the Definition and Classification of Cardiomyopathies, whole article).
Mewes & Ravens (1994) "L-type calcium currents of human myocytes from ventricle of nonfailing and failing hearts and from atrium" J. Mal. Cell. Cardiol. 26(10):1307-1320.
Missov et al. (1997) "Circulating cardiac troponin I in severe congestive heart failure" Circulation 96(9):2953-2958.
Mukherjee et al., "Changes in L-type calcium channel abundance and function during the transition to pacing-induced congestive heart failure", Cardiovasc Res., 1998, 37(2):432-444.
Muller et al., "Targeted disruption of the murine Bin1/Amphiphysin II gene does not disable endocytosis but results in embryonic cardiomyopathy with aberrant myofibril formation", Mol Cell Biol, (2003) 23: 4295-4306.
MyBioSource.com, "Anti-BIN1 Antibody:: Rabbit BIN1 Polyclonal Antibody", 2006, 1-4.
NCBI GenBank Accession No. NM_004305, Nov. 1, 2000.
Neufeld & White (1997) "Nuclear and cytoplasmic localizations of the adenomatous polyposis coli protein" Proc. Natl. Acad. Sci. U.S.A. 94(7):3034-3039.
Nicot et al., "Mutations in amphiphysin 2 (BIN1)disrupt interaction with dynamin 2 and cause autosomal recessive centronuclear myopathy," Nat. Genet., (2007), 39(9):1134-1139.
PCT International Search Report and Written Opinion dated Jun. 30, 2016 in PCT Application No. PCT/US2016/020495 (9 pages).
PCT International Search Report and Written Opinion for Application No. PCT/US2010/032282 dated Jan. 24, 2011. (7 pages).
PCT International Search Report and Written Opinion for Application No. PCT/US2011/059574 dated Jun. 20, 2012. (12 pages).
PCT Search Report and Written Opinion for Application No. PCT/US2011/057155 dated Mar. 2, 2012. (6 pages).
Pessah, et al. (1985) "The calcium-ryanodine receptor complex of skeletal and cardiac muscle" Biochem. Biophys. Res. Commun. 128(1):449-456.
Piot et al., "High frequency-induced up regulation of human cardiac calcium currents", Circulation, 1996, 93(1):120-8.
Pollack, A., "Doctors Seek Way to Treat Muscle Loss", The New York Times, Aug. 30, 2010; retrieved at http://www.nytimes.com/2010/08/31/health/research/31muscle.html.
Pollack, et al. (1997) "Dynamics of beta-catenin interactions with APC protein regulate epithelial tubulogenesis" J. Cell Biol. 137(7):1651-1662.
Ricchiuti et al. (1997) "Cardiac troponin I and T alterations in hearts with severe left ventricular remodeling" Clin Chem 43(6):990-995.

(56) References Cited

OTHER PUBLICATIONS

Schroder et al., "Increased availability and open probability of single L-type calcium channels from failing compared with nonfailing human ventricle", Circulation, 1998, 98(10):969-976.
Scriven, et al. (2000) "Distribution of proteins implicated in excitation-contraction coupling in rat ventricular myocytes" Biophys. J. 79(5):2682-2691.
Sedwick C., "BIN1: a protein with great heart", PLoS Biol., (Feb. 16, 2010), vol. 8, No. 2, pp. E1000311-1-E1000311-2.
Sen-Chowdhry et al. (2005) "Genetics of right ventricular cardiomyopathy" J Cardiovasc Electrophysiol 16(8):927-935.
Shaw, et al. (2007) "Microtubule plus-end-tracking proteins target gap junctions directly from the cell interior to adherens junctions" Cell 128(3):547-560.
Siew et al., "Biological Markers of Acute Kidney Injury", J Am Soc Nephrol, 22:810-820, 2011.
Sigma Clone 99 Antibody (1999, Product information retrieved from URL:www.sigmaaldrich.com/catalog/product/sigma/b9428?lang=en?ion=US.
Sipido, et al. (1998) "Frequency dependence of Ca2+ release from the sarcoplasmic reticulum in human ventricular myocytes from end-stage heart failure" Cardiovasc. Res. 37(2):478-488.
Slomianka, L., "Blue Histology—Muscle", School of Anatomy and Human Biology, The University of Western Australia, 2009, 1-14.
Stampfer et al., "Risk Factor Criteria", Circulation, 2004;109:IV-3-IV-5.
Takahashi, et al. (2004) "Membrane-associated guanylate kinase-like properties of betasubunits required for modulation of voltage-dependent Ca2+ channels" Proc. Natl. Acad. Sci. U.S.A. 101(18):7193-7198.
Tamura et al. (2000) "Cardiac fibrosis in mice lacking brain natriuretic peptide" Proc Natl Acad Sci USA 97(8):4239-4244.
Toussaint et al., "Defects in Amphiphysin 2 (BIN1) and Triads in Several Forms of Centronuclear Myopathies," Acta. Neuropathol., (2011), 121(2):253-266.
Wechsler-Reya et al., "A Role for the Putative Tumor Suppressor Bin1 in Muscle Cell Differentiation," Molecular and Cellular Biology, (1998), 18(1):566-575.
Westfall & Solaro (1992) "Alterations in myofibrillar function and protein profiles after complete global ischemia in rat hearts" Circ Res 70(2):302-313.
U.S. Notice of Allowance for U.S. Appl. No. 13/884,454 dated Oct. 4, 2017. (17 pages).
U.S. Notice of Allowance for U.S. Appl. No. 14/348,269 dated Aug. 16, 2017. (5 pages).
U.S. Office Action for U.S. Appl. No. 14/348,269 dated Sep. 22, 2016. (17 pages).
U.S. Office Action for U.S. Appl. No. 13/265,531 dated Mar. 29, 2013. (28 pages).
U.S. Office Action for U.S. Appl. No. 13/265,531 dated Oct. 24, 2013. (11 pages).
U.S. Office Action for U.S. Appl. No. 13/884,454 dated Dec. 11, 2015. (22 pages).
U.S. Office Action for U.S. Appl. No. 13/884,454 dated Dec. 23, 2016. (19 pages).
U.S. Office Action for U.S. Appl. No. 13/884,454 dated Jun. 15, 2017. (20 pages).
U.S. Office Action for U.S. Appl. No. 13/884,454 dated Jun. 4, 2015. (19 pages).
U.S. Office Action for U.S. Appl. No. 14/176,985 dated Jan. 26, 2015. (12 pages).
U.S. Office Action for U.S. Appl. No. 14/176,985 dated May 12, 2015. (7 pages).
U.S. Office Action for U.S. Appl. No. 14/348,269 dated Feb. 12, 2016. (15 pages).
U.S. Office Action for U.S. Appl. No. 14/348,269 dated Jun. 6, 2015. (8 pages).
U.S. Office Action for U.S. Appl. No. 14/348,269 dated Mar. 8, 2017. (12 pages).
U.S. Office Action for U.S. Appl. No. 14/348,269 dated Oct. 7, 2015. (29 pages).
U.S. Office Action for U.S. Appl. No. 14/626,546 dated Feb. 27, 2017. (35 pages).
U.S. Office Action for U.S. Appl. No. 14/626,546 dated Oct. 23, 2017. (20 pages).
U.S. Office Action for U.S. Appl. No. 15/555,043 dated Jun. 15, 2018. (18 pages).

```
79.38 identity in 608 residues overlap; Score: 1971.0; Gap frequency: 20.7%

▽
BIN1         1 NAEMGSKGVTAGKIASNVQKKLTRAQEKVLQKLGKADETKDEQFEQCVQNFNKQLTEGTR
BIN1+12a,    1 NAEMGSKGVTAGKIASNVQKKLTRAQEKVLQKLGKADETKDEQFEQCVQNFNKQLTEGTR
               ************************************************************

□
BIN1        61 LQKDLRTYLASVKAMHEASKKLNECLQEVYEPDWPGRDEANKIAENNDLLWMDYHCKLVD
BIN1+12a,   61 LQKDLRTYLASVKAMHEASKKLNECLQEVYEPDWPGRDEANKIAENNDLLWMDYHCKLVD
               ************************************************************

□              □  ▽ ▽                           □
BIN1       121 QALLTMDTYLGQFPDIKGRIAKFGRKLVDYDGARHHYESLQTAKKKDEAKIAKPVSLLEK
BIN1+12a,  121 QALLTMDTYLGQFPDIKGRIAKFGRKLVDYDGARHHYESLQTAKKKDEAKIAK-------
               *****************************************************

□                 □
BIN1       181 AAPQWCQGKLQAHLVAQTNLLRNQAEEELIKAQKVFEEMNVDLQEELPSLWNSRVGFYVN
BIN1+12a,  174 --------------------------AEEELIKAQKVFEEMNVDLQEELPSLWNSRVGFYVN
                                         ***********************************

□                        □
BIN1       241 TFQSIAGLEENFHKEMSKLNQNLNDVLVGLEKQHGSNTFTVKAQF---------------
BIN1+12a,  210 TFQSIAGLEENFHKEMSKLNQNLNDVLVGLEKQHGSNTFTVKAQPRKKSKLFSRLRRKKN
               ********************************************

BIN1       286 SDNAPAKGNKSPSPPDGSPAATPEIRVNHEPEPAGGATPGATLPKSPSQLRKGPPVPPPP
BIN1+12a,  270 SDNAPAKGNKSPSPPDGSPAATPEIRVNHEPEPAGGATPGATLPKSPSQ[LRKGPPVPPPP]
               ************************************************************

□
BIN1       346 KHTPSKEVKQEQILSLFEDTFVPEISVTTPSQFEAPGPFSEQASLLDLDFDPLPPVTSPV
BIN1+12a,  330 [KHTPSKEVKQEQILSLFEDTFVPEISVTTPSQ]---------------------------
             L ********************************

□
BIN1       406 KAPTPSGQSIPWDLWEPTESPAGSLPSGEPSAAEGTFAVSWPSQTAEPGPAQPAEASEVA
BIN1+12a,  362 ------------------------------------------------------PAEASEVA
                                                                     ********

BIN1       466 GGTQPAAGAQEPGETAASEAASSSLPAVVETFPATVNGTVEGGSGAGRLDLPPGFMFKV
BIN1+12a,  370 GGTQPAAGAQEPGETAASEAASSSLPAVVETFPATVNGTVEGGSGAGRLDLPPGFMFKV
               ***********************************************************

□□                                   ▽
BIN1       526 QAQHDYTATDTDELQLKAGDVVLVIPFQNPEEQDEGWLMGVKESDWNQHKELEKCRGVFP
BIN1+12a,  430 QAQHDYTATDTDELQLKAGDVVLVIPFQNPEEQDEGWLMGVKESDWNQHKELEKCRGVFP
               ************************************************************

BIN1       586 ENFTERVP  (SEQ ID NO: 19)    ▽ Germine Mutations    Exon 10
BIN1+12a,  490 ENFTERVP  (SEQ ID NO: 20)    □ Somatic Variations   [Exon 12a]
               ********
```

FIG. 2

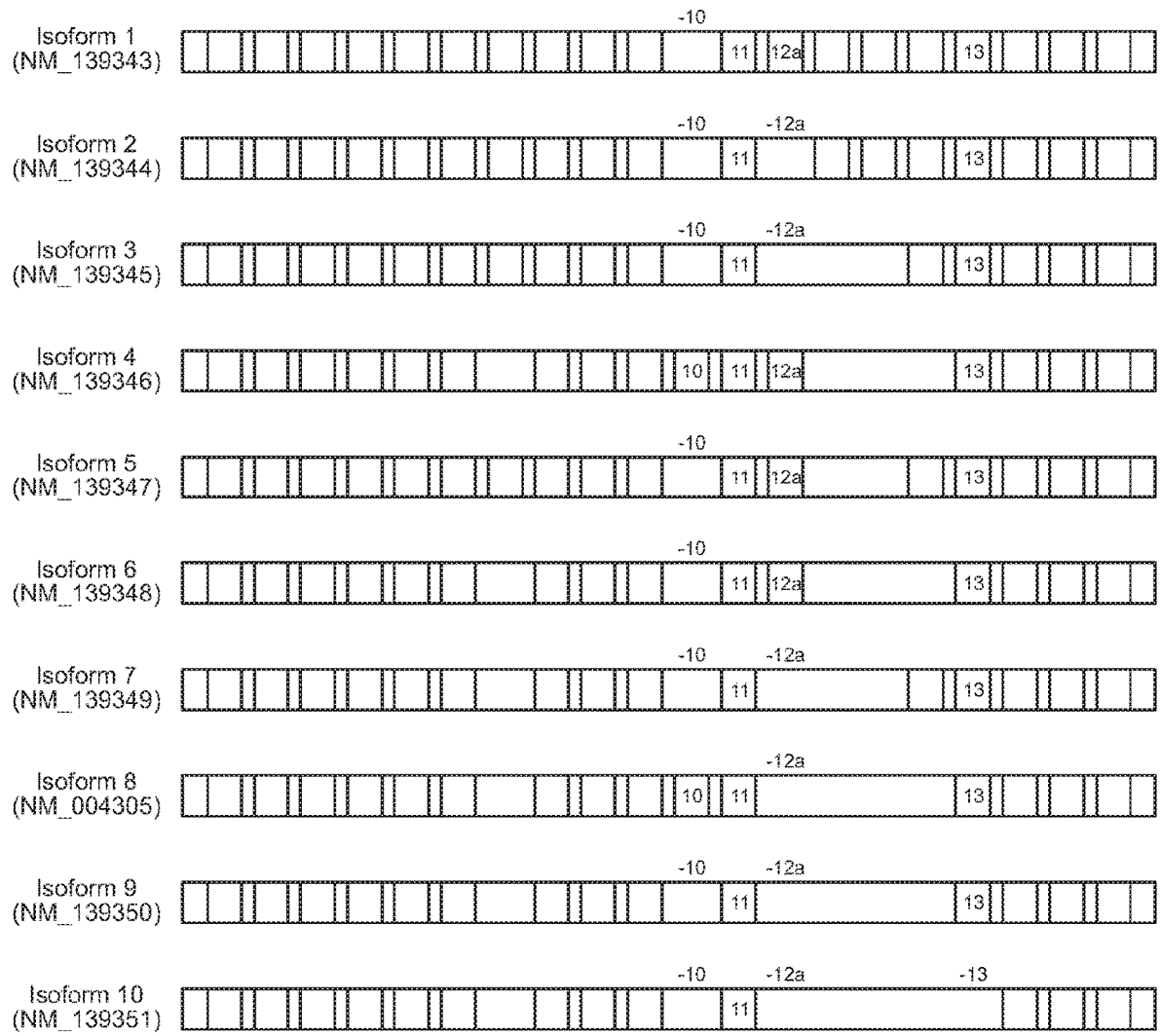
Bin1 cancer isoforms
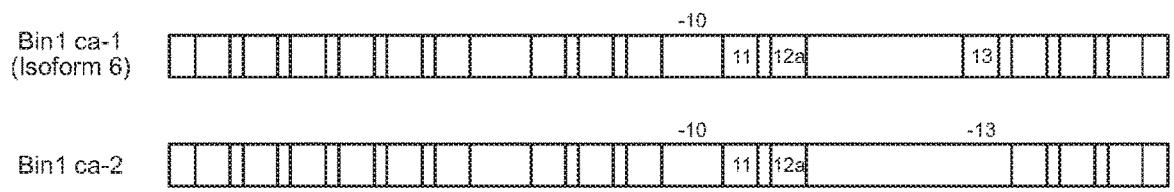
FIG. 3

SEQUENCE LISTING

```
<160> NUMBER OF SEQ ID NOS: 20

<210> SEQ ID NO 1
<211> LENGTH: 43
<212> TYPE: PRT
<213> ORGANISM: Homo sapiens

<400> SEQUENCE: 1

Leu Arg Lys Gly Pro Pro Val Pro Pro Pro Lys His Thr Pro Ser
1               5                   10                  15

Lys Glu Val Lys Gln Glu Gln Ile Leu Ser Leu Phe Glu Asp Thr Phe
            20                  25                  30

Val Pro Glu Ile Ser Val Thr Thr Pro Ser Gln
        35                  40

<210> SEQ ID NO 2
```

```
<211> LENGTH: 129
<212> TYPE: DNA
<213> ORGANISM: Homo sapiens

<400> SEQUENCE: 2
ctccggaaag gcccaccagt ccctccgcct cccaaacaca ccccgtccaa ggaagtcaag      60
caggagcaga tcctcagcct gtttgaggac acgtttgtcc ctgagatcag cgtgaccacc     120
ccctcccag                                                             129

<210> SEQ ID NO 3
<211> LENGTH: 550
<212> TYPE: PRT
<213> ORGANISM: Homo sapiens

<400> SEQUENCE: 3
```

Met Ala Glu Met Gly Ser Lys Gly Val Thr Ala Gly Lys Ile Ala Ser
1               5                   10                  15

Asn Val Gln Lys Lys Leu Thr Arg Ala Gln Glu Lys Val Leu Gln Lys
            20                  25                  30

Leu Gly Lys Ala Asp Glu Thr Lys Asp Glu Gln Phe Glu Gln Cys Val
        35                  40                  45

Gln Asn Phe Asn Lys Gln Leu Thr Glu Gly Thr Arg Leu Gln Lys Asp
    50                  55                  60

Leu Arg Thr Tyr Leu Ala Ser Val Lys Ala Met His Glu Ala Ser Lys
65                  70                  75                  80

Lys Leu Asn Glu Cys Leu Gln Glu Val Tyr Glu Pro Asp Trp Pro Gly
                85                  90                  95

Arg Asp Glu Ala Asn Lys Ile Ala Glu Asn Asn Asp Leu Leu Trp Met
            100                 105                 110

Asp Tyr His Gln Lys Leu Val Asp Gln Ala Leu Leu Thr Met Asp Thr
        115                 120                 125

Tyr Leu Gly Gln Phe Pro Asp Ile Lys Ser Arg Ile Ala Lys Arg Gly
    130                 135                 140

Arg Lys Leu Val Asp Tyr Asp Ser Ala Arg His His Tyr Glu Ser Leu
145                 150                 155                 160

Gln Thr Ala Lys Lys Lys Asp Glu Ala Lys Ile Ala Lys Pro Val Ser
                165                 170                 175

Leu Leu Glu Lys Ala Ala Pro Gln Trp Cys Gln Gly Lys Leu Gln Ala
            180                 185                 190

His Leu Val Ala Gln Thr Asn Leu Leu Arg Asn Gln Ala Glu Glu Glu
        195                 200                 205

Leu Ile Lys Ala Gln Lys Val Phe Glu Glu Met Asn Val Asp Leu Gln
    210                 215                 220

Glu Glu Leu Pro Ser Leu Trp Asn Ser Arg Val Gly Phe Tyr Val Asn
225                 230                 235                 240

Thr Phe Gln Ser Ile Ala Gly Leu Glu Glu Asn Phe His Lys Glu Met
                245                 250                 255

Ser Lys Leu Asn Gln Asn Leu Asn Asp Val Leu Val Gly Leu Glu Lys
            260                 265                 270

Gln His Gly Ser Asn Thr Phe Thr Val Lys Ala Gln Pro Ser Asp Asn
        275                 280                 285

Ala Pro Ala Lys Gly Asn Lys Ser Pro Ser Pro Pro Asp Gly Ser Pro
    290                 295                 300

Ala Ala Thr Pro Glu Ile Arg Val Asn His Glu Pro Glu Pro Ala Gly
305                 310                 315                 320

```
Gly Ala Thr Pro Gly Ala Thr Leu Pro Lys Ser Pro Ser Gln Phe Glu
                325                 330                 335

Ala Pro Gly Pro Phe Ser Glu Gln Ala Ser Leu Leu Asp Leu Asp Phe
            340                 345                 350

Asp Pro Leu Pro Pro Val Thr Ser Pro Val Lys Ala Pro Thr Pro Ser
        355                 360                 365

Gly Gln Ser Ile Pro Trp Asp Leu Trp Glu Pro Thr Glu Ser Pro Ala
    370                 375                 380

Ser Leu Pro Ser Gly Glu Pro Ser Ala Ala Glu Gly Thr Phe Ala
385                 390                 395                 400

Val Ser Trp Pro Ser Gln Thr Ala Glu Pro Gly Pro Ala Gln Pro Ala
                405                 410                 415

Glu Ala Ser Glu Val Ala Gly Gly Thr Gln Pro Ala Ala Gly Ala Gln
            420                 425                 430

Glu Pro Gly Glu Thr Ala Ala Ser Glu Ala Ala Ser Ser Ser Leu Pro
        435                 440                 445

Ala Val Val Val Glu Thr Phe Pro Ala Thr Val Asn Gly Thr Val Glu
    450                 455                 460

Gly Gly Ser Gly Ala Gly Arg Leu Asp Leu Pro Pro Gly Phe Met Phe
465                 470                 475                 480

Lys Val Gln Ala Gln His Asp Tyr Thr Ala Thr Asp Thr Asp Glu Leu
                485                 490                 495

Gln Leu Lys Ala Gly Asp Val Val Leu Val Ile Pro Phe Gln Asn Pro
            500                 505                 510

Glu Glu Gln Asp Glu Gly Trp Leu Met Gly Val Lys Glu Ser Asp Trp
        515                 520                 525

Asn Gln His Lys Glu Leu Glu Lys Cys Arg Gly Val Phe Pro Glu Asn
    530                 535                 540

Phe Thr Glu Arg Val Pro
545                 550

<210> SEQ ID NO 4
<211> LENGTH: 120
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Val Tyr Trp Val Lys Gln Arg Pro Glu Gln Gly Leu Glu Trp Ile
        35                  40                  45

Gly Trp Ile Asp Pro Glu Asn Gly Asn Thr Ile Tyr Asp Pro Glu Phe
    50                  55                  60

Gln Ala Lys Ala Ser Ile Thr Ala Asp Thr Ser Ser Asn Thr Ala Tyr
65                  70                  75                  80

Leu Gln Leu Ser Ser Leu Thr Ser Glu Gly Thr Ala Val Tyr Tyr Cys
                85                  90                  95

Val Arg Gly Glu Asp Tyr Gly Gly Tyr Ala Met Asp Tyr Trp Gly Gln
            100                 105                 110

Gly Thr Ser Val Thr Val Ser Ser
        115                 120
```

<210> SEQ ID NO 5
<211> LENGTH: 360
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 5
gaggtccagc tgcagcagtc tggggctgag cttgtgaggc caggggcctt agtcaagttg      60
tcctgcaaag cttctggctt caacattaaa gactactatg tgtattgggt gaagcagagg     120
cctgaacagg gcctggagtg gattggatgg attgatcctg agaatggtaa tactatatat     180
gacccggagt tccaggccaa ggccagtata acagcagaca catcctccaa cacagcctac     240
ctgcagctca gcagcctgac atctgagggc actgccgtct attactgtgt tagaggggag     300
gattacgggg gctatgctat ggactactgg ggtcaaggaa cctcagtcac cgtctcctca     360

<210> SEQ ID NO 6
<211> LENGTH: 112
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 6

Asp Ile Val Val Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Ser Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Phe Pro Phe Thr Phe Gly Ser Gly Thr Lys Leu Glu Ile Lys
            100                 105                 110

<210> SEQ ID NO 7
<211> LENGTH: 337
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7
gatattgtgg tgactcaggc tgcaccctct gtacctgtca ctcctggaga gtcagtttcc      60
atctcctgca ggtctagtaa gagtctcctg catagtaatg gcaacactta cttgtcttgg     120
ttcctgcaga ggccaggcca gtctcctcag ctcctgattt atcggatgtc caaccttgcc     180
tcaggagtcc cagacaggtt cagtggcagt gggtcaggca ctgctttcac actgagaatc     240
agtagagtga aggctgagga tgtgggtgtt tattactgta tgcaacatct agaatttccc     300
ttcacgttcg gctcggggac aaagttggaa ataaaac                              337

-continued

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 8

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Phe
                85                  90                  95

Thr Phe Gly Ser Gly Thr Lys Leu Glu Ile Lys
            100                 105

<210> SEQ ID NO 9
<211> LENGTH: 322
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 9
gacattgtga tgacccagtc tcacaaattc atgtccacat cagtaggaga cagggtcagc      60
atcacctgca aggccagtca ggatgtgagt actgctgtag cctggtatca acaaaaacca     120
gggcaatctc ctaaactact gatttactgg gcatccaccc ggcacactgg agtccctgat     180
cgcttcacag gcagtggatc tgggacagat tatactctca ccatcagcag tgtgcaggct     240
gaagacctgg cactttatta ctgtcagcaa cattatagca ctccattcac gttcggctcg     300
gggacaaagt tggaaataaa ac                                              322

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 10

Gly Phe Asn Ile Lys Asp Tyr Tyr
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      construct

```
<400> SEQUENCE: 11

Ile Asp Pro Glu Asn Gly Asn Thr
1               5

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 12

Val Arg Gly Glu Asp Tyr Gly Gly Tyr Ala Met Asp Tyr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 13

Lys Ser Leu Leu His Ser Asn Gly Asn Thr Tyr
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 14

Met Gln His Leu Glu Phe Pro Phe Thr
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 15

Gln Asp Val Ser Thr Ala
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 16

Gln Gln His Tyr Ser Thr Pro Phe Thr
1               5

<210> SEQ ID NO 17
<211> LENGTH: 3
<212> TYPE: PRT
```

```
<213> ORGANISM: Artificial Sequence
<220> FEATURE:
<223> OTHER INFORMATION: Description of Artificial Sequence: Synthetic
      construct

<400> SEQUENCE: 17

Arg Met Ser
1

<210> SEQ ID NO 18
<211> LENGTH: 3
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 18

Trp Ala Ser
1

<210> SEQ ID NO 19
<211> LENGTH: 593
<212> TYPE: PRT
<213> ORGANISM: Homo sapiens

<400> SEQUENCE: 19

Asn Ala Glu Met Gly Ser Lys Gly Val Thr Ala Gly Lys Ile Ala Ser
1               5                   10                  15

Asn Val Gln Lys Lys Leu Thr Arg Ala Gln Glu Lys Val Leu Gln Lys
            20                  25                  30

Leu Gly Lys Ala Asp Glu Thr Lys Asp Glu Gln Phe Glu Gln Cys Val
        35                  40                  45

Gln Asn Phe Asn Lys Gln Leu Thr Glu Gly Thr Arg Leu Gln Lys Asp
    50                  55                  60

Leu Arg Thr Tyr Leu Ala Ser Val Lys Ala Met His Glu Ala Ser Lys
65                  70                  75                  80

Lys Leu Asn Glu Cys Leu Gln Glu Val Tyr Glu Pro Asp Trp Pro Gly
                85                  90                  95

Arg Asp Glu Ala Asn Lys Ile Ala Glu Asn Asn Asp Leu Leu Trp Met
            100                 105                 110

Asp Tyr His Cys Lys Leu Val Asp Gln Ala Leu Leu Thr Met Asp Thr
        115                 120                 125

Tyr Leu Gly Gln Phe Pro Asp Ile Lys Gly Arg Ile Ala Lys Phe Gly
    130                 135                 140

Arg Lys Leu Val Asp Tyr Asp Gly Ala Arg His His Tyr Glu Ser Leu
145                 150                 155                 160

Gln Thr Ala Lys Lys Lys Asp Glu Ala Lys Ile Ala Lys Pro Val Ser
                165                 170                 175

Leu Leu Glu Lys Ala Ala Pro Gln Trp Cys Gln Gly Lys Leu Gln Ala
            180                 185                 190

His Leu Val Ala Gln Thr Asn Leu Leu Arg Asn Gln Ala Glu Glu Glu
        195                 200                 205

Leu Ile Lys Ala Gln Lys Val Phe Glu Glu Met Asn Val Asp Leu Gln
    210                 215                 220

Glu Glu Leu Pro Ser Leu Trp Asn Ser Arg Val Gly Phe Tyr Val Asn
225                 230                 235                 240

Thr Phe Gln Ser Ile Ala Gly Leu Glu Glu Asn Phe His Lys Glu Met
                245                 250                 255
```

```
Ser Lys Leu Asn Gln Asn Leu Asn Asp Val Leu Val Gly Leu Glu Lys
            260                 265                 270

Gln His Gly Ser Asn Thr Phe Thr Val Lys Ala Gln Phe Ser Asp Asn
        275                 280                 285

Ala Pro Ala Lys Gly Asn Lys Ser Pro Ser Pro Asp Gly Ser Pro
290                 295                 300

Ala Ala Thr Pro Glu Ile Arg Val Asn His Glu Pro Glu Pro Ala Gly
305                 310                 315                 320

Gly Ala Thr Pro Gly Ala Thr Leu Pro Lys Ser Pro Ser Gln Leu Arg
                325                 330                 335

Lys Gly Pro Pro Val Pro Pro Pro Lys His Thr Pro Ser Lys Glu
                340                 345                 350

Val Lys Gln Glu Gln Ile Leu Ser Leu Phe Glu Asp Thr Phe Val Pro
            355                 360                 365

Glu Ile Ser Val Thr Thr Pro Ser Gln Phe Glu Ala Pro Gly Pro Phe
        370                 375                 380

Ser Glu Gln Ala Ser Leu Leu Asp Leu Asp Phe Asp Pro Leu Pro Pro
385                 390                 395                 400

Val Thr Ser Pro Val Lys Ala Pro Thr Pro Ser Gly Gln Ser Ile Pro
                405                 410                 415

Trp Asp Leu Trp Glu Pro Thr Glu Ser Pro Ala Gly Ser Leu Pro Ser
                420                 425                 430

Gly Glu Pro Ser Ala Ala Glu Gly Thr Phe Ala Val Ser Trp Pro Ser
            435                 440                 445

Gln Thr Ala Glu Pro Gly Pro Ala Gln Pro Ala Glu Ala Ser Glu Val
        450                 455                 460

Ala Gly Gly Thr Gln Pro Ala Ala Gly Ala Gln Glu Pro Gly Glu Thr
465                 470                 475                 480

Ala Ala Ser Glu Ala Ala Ser Ser Ser Leu Pro Ala Val Val Val Glu
                485                 490                 495

Thr Phe Pro Ala Thr Val Asn Gly Thr Val Glu Gly Gly Ser Gly Ala
                500                 505                 510

Gly Arg Leu Asp Leu Pro Pro Gly Phe Met Phe Lys Val Gln Ala Gln
            515                 520                 525

His Asp Tyr Thr Ala Thr Asp Thr Asp Glu Leu Gln Leu Lys Ala Gly
        530                 535                 540

Asp Val Val Leu Val Ile Pro Phe Gln Asn Pro Glu Glu Gln Asp Glu
545                 550                 555                 560

Gly Trp Leu Met Gly Val Lys Glu Ser Asp Trp Asn Gln His Lys Glu
                565                 570                 575

Leu Glu Lys Cys Arg Gly Val Phe Pro Glu Asn Phe Thr Glu Arg Val
                580                 585                 590

Pro

<210> SEQ ID NO 20
<211> LENGTH: 497
<212> TYPE: PRT
<213> ORGANISM: Homo sapiens

<400> SEQUENCE: 20

Asn Ala Glu Met Gly Ser Lys Gly Val Thr Ala Gly Lys Ile Ala Ser
1               5                   10                  15

Asn Val Gln Lys Lys Leu Thr Arg Ala Gln Glu Lys Val Leu Gln Lys
            20                  25                  30
```

```
Leu Gly Lys Ala Asp Glu Thr Lys Asp Glu Gln Phe Glu Gln Cys Val
        35                  40                  45
Gln Asn Phe Asn Lys Gln Leu Thr Glu Gly Thr Arg Leu Gln Lys Asp
    50                  55                  60
Leu Arg Thr Tyr Leu Ala Ser Val Lys Ala Met His Glu Ala Ser Lys
65                  70                  75                  80
Lys Leu Asn Glu Cys Leu Gln Glu Val Tyr Glu Pro Asp Trp Pro Gly
                85                  90                  95
Arg Asp Glu Ala Asn Lys Ile Ala Glu Asn Asn Asp Leu Leu Trp Met
                100                 105                 110
Asp Tyr His Cys Lys Leu Val Asp Gln Ala Leu Leu Thr Met Asp Thr
            115                 120                 125
Tyr Leu Gly Gln Phe Pro Asp Ile Lys Gly Arg Ile Ala Lys Phe Gly
        130                 135                 140
Arg Lys Leu Val Asp Tyr Asp Gly Ala Arg His His Tyr Glu Ser Leu
145                 150                 155                 160
Gln Thr Ala Lys Lys Asp Glu Ala Lys Ile Ala Lys Ala Glu Glu
                165                 170                 175
Glu Leu Ile Lys Ala Gln Lys Val Phe Glu Glu Met Asn Val Asp Leu
            180                 185                 190
Gln Glu Glu Leu Pro Ser Leu Trp Asn Ser Arg Val Gly Phe Tyr Val
        195                 200                 205
Asn Thr Phe Gln Ser Ile Ala Gly Leu Glu Glu Asn Phe His Lys Glu
    210                 215                 220
Met Ser Lys Leu Asn Gln Asn Leu Asn Asp Val Leu Val Gly Leu Glu
225                 230                 235                 240
Lys Gln His Gly Ser Asn Thr Phe Thr Val Lys Ala Gln Pro Arg Lys
                245                 250                 255
Lys Ser Lys Leu Phe Ser Arg Leu Arg Arg Lys Lys Asn Ser Asp Asn
                260                 265                 270
Ala Pro Ala Lys Gly Asn Lys Ser Pro Ser Pro Pro Asp Gly Ser Pro
        275                 280                 285
Ala Ala Thr Pro Glu Ile Arg Val Asn His Gly Pro Glu Pro Ala Gly
    290                 295                 300
Gly Ala Thr Pro Gly Ala Thr Leu Pro Lys Ser Pro Ser Gln Leu Arg
305                 310                 315                 320
Lys Gly Pro Pro Val Pro Pro Pro Lys His Thr Pro Ser Lys Glu
                325                 330                 335
Val Lys Gln Glu Gln Ile Leu Ser Leu Phe Glu Asp Thr Phe Val Pro
        340                 345                 350
Glu Ile Ser Val Thr Thr Pro Ser Gln Pro Ala Glu Ala Ser Glu Val
    355                 360                 365
Ala Gly Gly Thr Gln Pro Ala Ala Gly Ala Gln Glu Pro Gly Glu Thr
370                 375                 380
Ala Ala Ser Glu Ala Ala Ser Ser Ser Leu Pro Ala Val Val Val Glu
385                 390                 395                 400
Thr Phe Pro Ala Thr Val Asn Gly Thr Val Glu Gly Gly Ser Gly Ala
                405                 410                 415
Gly Arg Leu Asp Leu Pro Pro Gly Phe Met Phe Lys Val Gln Ala Gln
            420                 425                 430
His Asp Tyr Thr Ala Thr Asp Thr Asp Glu Leu Gln Leu Lys Ala Gly
        435                 440                 445
```

-continued

```
Asp Val Val Leu Val Ile Pro Phe Gln Asn Pro Glu Gln Asp Glu
    450                 455             460

Gly Trp Leu Met Gly Val Lys Glu Ser Asp Trp Asn Gln His Lys Glu
465             470                 475             480

Leu Glu Lys Cys Arg Gly Val Phe Pro Glu Asn Phe Thr Glu Arg Val
                485             490                 495

Pro
```

BIN1 EXPRESSION AS A MARKER OF CANCER

CROSS-REFERENCE TO RELATED APPLICATIONS

This application a Continuation of U.S. application Ser. No. 14/348,269, filed Mar. 28, 2014, which is now U.S. Pat. No. 9,846,159, issued on Dec. 19, 2017; which is a U.S. national stage application of International Patent Application No. PCT/US2012/058051, filed on Sep. 28, 2012, which claims benefit of U.S. Provisional Application No. 61/541,539, filed Sep. 30, 2011, each of which is hereby incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 19, 2020, is named 113310-0146_SL.txt and is 22,390 bytes in size.

BACKGROUND

Cancer is one of the leading causes of death in the United States. Early diagnosis of cancer and effective monitoring of metastasis and treatment effects can assist in risk stratification and in guiding therapy.

SUMMARY

Provided are methods of screening a subject for cancer. The methods comprise obtaining a blood sample from the subject and detecting in the sample a level of Bridging Integrator 1 (BIN1) isoforms that contain polypeptide encoded by exon 12a (i.e., 12a+ BIN1). An elevated level of 12a+ BIN1 isoforms in the blood sample, as compared to a negative control level, indicates the subject has cancer. Therefore, if the subject has an elevated level of 12a+ BIN1 isoforms, the method can further comprise obtaining a tissue sample from the subject, e.g., for histological examination or other analysis for the purpose of confirming and further defining the cancer.

There are at least five isoforms of BIN1 that contain polypeptides encoded by exon 12a: isoforms 1, 4, 5, 6 (also referred to herein as Ca-1), and the isoform referred to herein as Ca-2. The disclosed method can therefore involve determining the level of a subset of BIN1 isoforms, including the levels of Ca-1, Ca-2, or a combination thereof. Therefore, the disclosed method can involve determining the Ca-1 and/or Ca-2 isoform level in the blood sample.

Also provided are methods for determining efficacy of a cancer therapy in a subject based on changes in levels of the Ca-1 and Ca-2 BIN1 isoforms. The methods can therefore comprise obtaining a first blood sample from a subject with cancer prior to treatment with a first cancer therapy, determining a first level of Ca-1 and/or Ca-2 isoform in the first blood sample, obtaining a second blood sample from a subject with cancer after at least one treatment with the first cancer therapy, determining a second level of Ca-1 and/or Ca-2 isoform in the second blood sample, and comparing the first level to the second level. In these methods, if the Ca-1 and/or Ca-2 isoform value increases or fails to decrease in the second blood sample as compared to the first blood sample, a second cancer therapy can be selected for the subject, which includes supplementing or replacing the cancer therapy with additional or alternative surgery, chemotherapy, or radiation therapy. For example, dosage of a chemotherapeutic can be increased. If the Ca-1 and/or Ca-2 isoform value decreases in the second blood sample as compared to the first blood sample, treatment of the subject with the first cancer therapy can be continued. If the Ca-1 and/or Ca-2 isoform value is sufficiently reduced, therapy may be discontinued or maintenance therapy initiated. This method can be repeated for each subsequent cancer therapy. The level of the Ca-1 and/or Ca-2 isoforms is an indication of cancer burden, thereby allowing for quantification of disease and effectiveness of cancer therapy.

Further provided are methods of treating cancer in a subject. The methods comprise determining levels of Ca-1 and/or Ca-2 isoform in a first blood sample from a subject with cancer, providing a first treatment to the subject, determining levels of Ca-1 and/or Ca-2 isoform in a second blood sample from the subject, and providing a second treatment to the subject based on whether the level of Ca-1 and/or Ca-2 isoform in the second blood sample is higher, lower, or the same as the level of expression in the first blood sample.

Also provided is a method of treating cancer in a subject by selecting a subtype of cancer showing an elevated Ca-1 and/or Ca-2 isoform level and providing a therapy that addresses the BIN1 pathway. The methods comprise obtaining a blood sample from the subject, determining a level of Ca-1 and/or Ca-2 isoform in the blood sample, comparing the Ca-1 and/or Ca-2 isoform level to one or more control levels, and administering to the subject an inhibitor of indoleamine 2, 3-dioxygenase (IDO) if an elevated Ca-1 and/or Ca-2 isoform level is determined.

Also provided is an isolated antibody that selectively binds the polypeptide encoded by exon 12a of human BIN1 (12a+ BIN1). Kits containing this antibody are also provided for detecting Ca-1 and/or Ca-2 isoform levels. The kit can contain an assay system for detecting 12a+ BIN1, an assay system for detecting 12a+/13+ BIN1, and/or an assay system for detecting 10+/12a BIN1.

The details of one or more embodiments are set forth in the accompanying drawings and the description below. Other features, objects, and advantages will be apparent from the description and drawings, and from the claims.

DESCRIPTION OF DRAWINGS

FIG. 2 is a sequence alignment of BIN1 isoform 1 and isoform 4, which both contain exon 12a.

FIG. 3 is an illustration of the BIN1 isoforms based on the presence or absence of exons due to alternative splicing.

FIG. 11A shows results for animals #1 to #4 having a pre-treatment signal >15. FIG. 11B shows results for animals #5 to #8 having a pre-treatment signal <15 but >2. FIG. 11C shows results for animals #9 to #11 having a pre-treatment signal >2.

Figure 1:
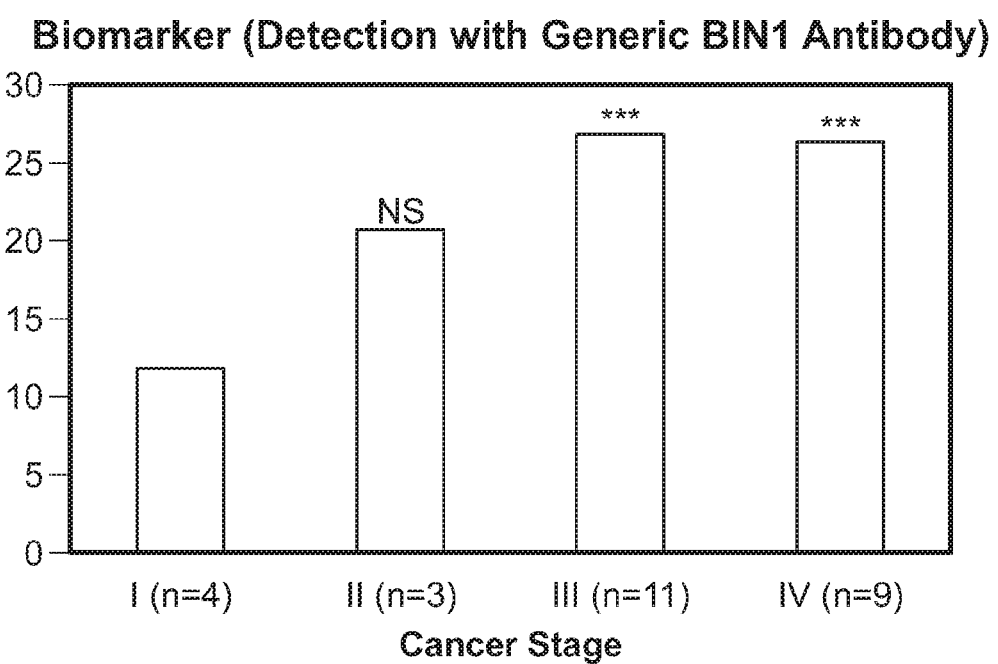
FIG. 1 shows a histogram showing that serum BIN1 is increased in canines with advanced stages of cancer. Detection is based on total BIN1. *** $P<0.001$.

The Bridging integrator 1 (BIN1) gene encodes several isoforms of a nucleocytoplasmic protein through alternative splicing. Ten BIN1 isoforms have been identified to date with two isoforms being ubiquitously expressed while others are present only in specific tissues. Among different functions, BIN1 acts as a tumor suppressor through binding the oncogenic protein c-Myc. Accordingly, several studies have shown a decrease in BIN1 expression during cancer progression. Interestingly, there is increasing evidence that aberrant splicing of BIN1 and a consequently increase in the expression of specific isoform(s) correlates with cancer progression. Using public databases listed in Table 1, a study was performed to capture the sequence of the isoform 4 of BIN1 to identify germline and somatic mutations that can occur in the BIN1 sequence, and identifying correlations between alternate BIN1 splicing and expression during human disease progression.

TABLE 1

| Databases used for BIN1 analysis | |
| --- | --- |
| ONIM (Online Mendelian Inheritance in Man) | Online Catalog of Human Genes and Genetic Disorders |
| HGMD (The Human Gene Mutation Database) | Resource providing comprehensive data on human inherited disease mutations to genetics and genomic research. |
| GWAS (Genome-wide association studies) | Used to identify common genetic factors that influence health and disease. |
| TCGA (The Cancer Genome Atlas) | Platform to search, download, and analyze data sets |
| COSMIC (Catalogue Of Somatic Mutations In Cancer) | Store and display somatic mutation information and related details and contains information relating to human cancers |
| HPRD (Human Protein Reference Database) | Platform to visually depict and integrate information pertaining to domain architecture, post-translational modifications, interaction networks and disease association for each protein in the human proteome. |
| Alamut | Application that integrates genetic information from different sources in one, consistent and convenient environment to describe variants using HGVS nomenclature and help interpret. their pathogenic status. |
| LOVD (Leiden Open Variation Database) | Provide a flexible, freely available tool for Gene-centered collection and display of DNA variations. |
| CancerGEM KB (Cancer Genomic Evidence-based Medicine Knowledge Base) | An integrated, searchable knowledge base of cancer human genome epidemiology and genomic applications in cancer care and prevention |
| DGV (Database of Genomic Variants) | A curated catalogue of structural variation in the human genome |
| GEO (Gene Expression Omnibus) | Public functional genomics data repository supporting Minimum Information About a Microarray Experiment-compliant data submissions. |
| KEGG (Kyoto Encyclopedia of Genes and Genomes) | Bioinformatics resource for linking genomes to life and the environment. |
| Others: NCBI, Ensembl, UnitProtKB, and GeneCards | |

DETAILED DESCRIPTION

Methods described herein are based on the finding that cancer can be detected in a subject by detecting in a blood sample from the subject elevated levels of a subset of BIN1 isoforms that contain the polypeptide encoded by exon 12a (12a+ BIN1). An elevated level of 12a+ BIN1 isoforms in a blood sample from the subject, as compared to a negative control level, indicates the subject has cancer. Accordingly, 12a+ BIN1 expression can be used as a marker to determine a diagnosis of cancer in the subject, determine the level of progression or metastatic potential of the cancer in the subject, and to follow the disease in the subject. Furthermore, 12a+ BIN1 expression can be used to determine the subtype of cancer in a subject as a means of selecting an effective therapy, including for example, an agent that affects the BIN1 pathway.

The BIN1 gene is located on chromosome 2 (2q14) between 127,805,599 and 127,864,903 bps (source: NCBI), and comprises 20 exons which can be alternatively spliced to form at least ten different isoforms. The BIN1 protein contains distinct domains such as a BAR domain (BIN1-amphiphysin-Rvs167), a phosphoinositide-binding domain, a clathrin-associated protein-binding domain (CLAP), a Myc-binding domain (MBD), and a Src homology 3 domain (SH3) (Prendergast G C, et al., *Biochim Biophys Acta.* 2009 1795(1):25-36). The exon 12a encodes a part of the CLAP domain. Four isoforms of BIN1 contain the exon 12a including the longest isoform of BIN1 (variant 1: GenBank accession number AF004015) and BIN1+12a, also named transcript variant 4 (GenBank accession number AF068918, NM_139346, NP_647596). BIN1+12a lacks four in-frame exons and has an additional in-frame exon (exon 10) in the coding region, compared to BIN1 variant 1. A sequence alignment of BIN1 variant 1 and variant 4 is provided in FIG. 2. BIN1 variant 1 and variant are expressed predominantly in the central nervous system.

Several genetic mutations in the BIN1 gene have been associated with the muscle weakness disorder centronuclear myopathy. These mutations include a homozygous 105G-T transversion in the BIN1 gene, resulting in a lys35-to-asn (K35N) substitution, and a homozygous 451G-A transition resulting in an asp151-to-asn (D151N) substitution. In addition, a mutation which generates a prematurely terminated BIN1 protein was also identified with a homozygous 1723A-T transversion in the BIN1 gene, resulting in a lys575-to-ter (K575X) substitution. Finally, a homozygous 461G-A transition in exon 6 of the BIN1 gene, resulting in an arg154-to-gin (R154Q) substitution was also identified in a patient with autosomal recessive centronuclear myopathy. The isoform 8 of BIN1 (GenBank accession number AF068918), a variant which lacks five in-frame exons including exon 12a and has an additional in-frame exon (exon 10) in the coding region compared to BIN1 variant 1, is specifically expressed in skeletal muscle. Alternative splicing of this isoform 8, leading to the exclusion of exon 10 (phosphoinositide-binding domain) is associated with muscle weakness in Myotonic dystrophy. Finally, several single nucleotide polymorphisms (SNPs) have been described in the BIN1 gene, including two in exon 12a. No phenotypes have been identified with these two SNPs.

BIN1 acts as a tumor suppressor through binding to c-Myc and subsequently repressing its transcriptional activity. Accordingly, attenuated expression of BIN1 is observed in many cases of breast, prostate, lung, brain, and colon cancers. Interestingly, cancer-specific variants of the ubiquitous isoforms 9 and 10 present an aberrant inclusion of the CNS-specific exon 12a. 12a+ BIN1 isoforms are observed in many tumor cells and tumor cell lines, and represent a common missplicing events occurring in human cancer (Prendergast G C, et al., *Biochim Biophys Acta*. 2009 1795(1):25-36). For example, these 12a+ BIN1 isoforms are aberrantly expressed in melanoma and this alternative splicing abolishes the tumor suppressor activity of BIN1 allowing c-Myc overexpression without induction of programmed cell death (Ge K, et al., *Proc. Natl. Acad. Sci. U.S.A.* 1999 96(17):9689-94; Xu Q, et al., *Nucleic Acids Res.* 2003 31(19):5635-43).

Somatic mutations in the BIN1 gene, both missense and synonymous, have also been reported in several cases of cancer including skin (in 3 out of 8 samples), brain (2/469), lung (1/11), ovary (3/3), large intestine (2/14), and prostate (3/4) cancers.

In addition, increases in BIN1 levels have been observed in different types of cancer or during cancer progression. Gene array analysis of the SW480 colon carcinoma cell line, and their relative lymph node metastatic SW620 cells showed statistically significant increase in BIN1 transcript level in the metastatic cells SW620 compared to the SW480 cells isolated from the primary tumor. In another study in which 22 primary human advanced gastric cancer tissues and 8 noncancerous gastric tissues were analyzed by high-density oligonucleotide, the level of BIN1 transcript was higher in 40% of patient cancer tissues compare to normal gastric tissues. Other studies measured the expression of the BIN1 protein in tissues of patients with different cancers using antibodies against the N-terminal or the C-terminal domain of BIN1. The results showed strong expression of BIN1 in malignant lymphoma (in 75% of cases), in malignant glioma (48%), and in testis cancer (43%). In addition, a moderate to strong staining was observed in cancer tissues of patients with colorectal (in 73% of cases), prostate (100%), ovarian (62%), skin (66%), renal (75%), and lung (46%) cancers. (source: HPRD).

Thus, the bridging integrator 1 (BIN1) gene encodes a nucleocytosolic protein that was initially identified as a Myc-interacting protein with features of a tumor suppressor. BIN1 is also known as amphiphysin II, amphiphysin-like, and box dependent MYC interacting protein 1. Alternative splicing of the BIN1 pre-mRNA transcript results in at least eleven transcript variants encoding different isoforms. Some isoforms of BIN1 are expressed ubiquitously, while others show a tissue specific expression. BIN1 isoforms 1-7 are expressed in neurons. Isoform 8 is skeletal muscle specific, while isoforms 9 and 10 are ubiquitous. Isoforms that are expressed in the central nervous system may be involved in synaptic vesicle endocytosis and may interact with dynamin, synaptojanin, endophilin, and clathrin. Aberrant splice variants expressed in tumor cell lines have also been described, which include isoforms that include exon 12a that is normally spliced into BIN1 mRNA with other exons (exons 12b-12d) in the central nervous system. Exon 12a can have the following nucleotide sequence: 5'-CTCCGGAAAG GCCCACCAGT CCCTCCGCCT CCCAAACACA CCCCGTCCAA GGAAGTCAAG CAGGAGCAGA TCCTCAGCCT GTTTGAGGAC ACGTTTGTCC CTGAGATCAG CGTGACCACC CCCTCCCAG-3' (SEQ ID NO:2). Alternatively, the nucleotide sequence shows at least 85, 90, or 95 percent identity to SEQ ID NO:2 and such variations may or may not result in amino acid changes in the expressed protein.

BIN1 is generally considered a tumor suppressor. However BIN1 protein isoforms containing 12a act as a tumor-promotor. Without exon 12a, BIN1 is a tumor suppressor by sequestering myc through its myc-binding domain, which is encoded by exons 13 and 14. However, on malignant transformation, 12a+ BIN1 does not sequester the Myc oncogene, freeing Myc to drive the cells into proliferation. Thus an assay specific for 12a+ BIN1 can detect a physiological state in which cancer BIN1 predominates and/or is active.

There are at least five isoforms of BIN1 that contain the polypeptide encoded by exon 12a (12a+ BIN1): isoforms 1, 4, 5, 6 (also referred to herein as Ca-1), and the isoform referred to herein as Ca-2. As disclosed herein, presence of the Ca-1 and/or Ca-2 isoforms are particularly indicative of cancer. The disclosed method can therefore involve determining the level of a subset of BIN1 isoforms, including the levels of Ca-1, Ca-2, or a combination thereof. Therefore, the disclosed method can involve determining the Ca-1 and/or Ca-2 isoform level in the blood sample.

Isoform Ca-2 differs from isoforms 1, 4, 5, and 6 by the absence of the polypeptide encoded by exon 13. Therefore, the disclosed method can further involve detecting a blood level of BIN1 isoforms that contain a polypeptide encoded by at least both exon 12a and exon 13 (i.e., 12a+/13+ BIN1), thereby excluding the Ca-2 isoform. The ratio or the difference of all 12a+ BIN1 isoforms to that of the 12a+/13+ subset determines the level of the Ca-2 (i.e., 12a+/13− BIN1) isoform. Ca-1 levels can likewise be specifically determined by, for example, detecting a polypeptide encoded by at least exons 10 and 12a of BIN1.

Reference therefore to determination of Ca-1 and/or Ca-2 isoform levels as used throughout includes the detection of 12a+ BIN1 (i.e., polypeptides encoded by exon 12a) and optional detection of 13+ BIN (i.e., polypeptides encoded by exon 13a) and/or 10+ BIN1 (i.e., polypeptides encoded by exon 10) to isolate and determine levels of Ca-1 (10+/12a+ BIN1) and/or Ca-2 (12a+/13− BIN1) isoforms.

Provided herein are methods of diagnosing cancer in a subject. The methods comprise obtaining a blood sample from the subject and detecting a level of Ca-1 and/or Ca-2 isoforms in the sample. An elevated level of Ca-1 and/or Ca-2 isoforms, particularly levels of the Ca-2 isoform, above a control level indicates that the subject has cancer. Therefore, if the subject has an elevated level of Ca-1 and/or Ca-2 isoforms, the method can further comprise obtaining a tissue sample (biopsy) from the subject, e.g., for histological examination, or other analysis for the purpose of confirming and further defining the cancer. Other steps of diagnosis are known to those of skill in the art and include additional laboratory tests (e.g., additional blood tests, urine tests, or tissue analysis using the same BIN1 markers or other markers), imaging, and the like. Blood tests that can be used concurrently or subsequent to the BIN1 analysis include analysis of prostate-specific antigen (PSA), cancer antigen 125 (CA125), calcitonin, alpha fetoprotein (AFP), human chorionic gonadotropin (HCG), and others. In addition, if the subject has elevated level of Ca-1 and/or Ca-2 isoforms, the method can further comprises imaging the subject to confirm the presence of cancer. Diagnostic imaging techniques for cancer include X-ray, CT, PET. MRI, and ultrasound.

The disclosed method can involve detecting the level of a subset of the 12a+ BIN1 isoforms, including the levels of Ca-1, Ca-2, or a combination thereof. Therefore, the disclosed method can comprise detecting a level of 12a+/13− (Ca-2) BIN1 isoform in the sample and comparing it to a control level. Therefore, the method can comprise obtaining a blood sample from the subject, detecting a level of 12a+ BIN1 isoforms in the sample, detecting a level of 12a+/13a+ BIN1 isoforms in the sample, comparing the detected level of 12a+ BIN1 isoforms to the detected level of 12a+/13a+ BIN1 isoforms to determine an 12a+/13− BIN1 (Ca-2) value for the sample, and comparing the 12a+/13− BIN1 (Ca-2) value to one or more control values. In these methods, an elevated 12a+/13− BIN1 (Ca-2) value indicates the subject has a cancer or a likelihood of cancer such that the subject requires additional testing. Therefore, if the subject has an elevated 12a+/13− BIN1 (Ca-2) value, the method can further comprise obtaining a tissue sample from the subject, e.g., for histological examination, or other analysis for the purpose of confirming and further defining the cancer as described above.

Control levels can be used to establish a threshold value. e.g., such that a Ca-1 and/or Ca-2 value greater than the threshold value indicates the subject has cancer. This threshold value can be determined empirically by comparing positive controls (samples from subjects with cancer or a particular type or stage of cancer) and negative controls (samples of subjects without cancer or who have been successfully treated for cancer). Such controls are optionally age matched or matched according to cancer type or stage. In order to distinguish elevated Ca-1 and/or Ca-2 values, the threshold value can be set at least 1, 1.5, 2, 2.5, 3, 3.5, 4, 4.5, or 5 standard deviations above the mean negative control value. Other statistical methods can be used to set a threshold value that is within the desired predictive power needed for the assay. For example, the threshold value can be set such that there is no statistically significant difference between the threshold value and the positive control values using routine statistical analysis.

As used herein, a negative control level can be determined from a different subject(s) without cancer, or the same subject(s) prior to the diagnosis of cancer. Likewise, a positive control value can be determined from one or more subjects with cancer. Alternatively, the positive control can be based on one or more samples containing known concentrations of BIN1 isoform(s), such as recombinant BIN1, as in a standard control.

Optionally, the 12a+ BIN1 polypeptide sequence comprises the amino acid sequence LRKGPPVPPP PKHTPSKEVK QEQILSLFED TFVPEISVTT PSQ (SEQ ID NO:1). Alternatively, the amino acid sequence can be at least 85, 90, or 95 percent identical to SEQ ID NO:1. Variations in the sequence can include amino acid insertions, deletions, or substitutions (including, for example, 1-5 conservative amino acid substitutions).

Optionally, the cancer is a solid tumor (e.g., a carcinoma, melanoma, sarcoma, lymphoma, or neuroblastoma) or a blood-based cancer (e.g., leukemia or lymphoma). The cancer can, for example, be a primary cancer or a metastatic cancer. The cancer can be selected from the group consisting of a lymphosarcoma, a lymphosarcoma, an oral Sarcoma, a soft tissue sarcoma, or a mast cell tumor. The cancer can be selected from the group consisting of a melanoma, a lymphoma, a myoma, a myosarcoma, a round cell tumor, an adenocarcinoma, a fibrosarcoma, or an adenosarcoma. The cancer can be selected from the group consisting of a myelolipoma, osteosarcoma, hemangiosarcoma, sebaceous cancer, hepatic adenoma, and fibrosarcoma. The cancer can be selected from the group consisting of a lung cancer, breast cancer, brain cancer, liver cancer, prostate cancer, colon cancer, gastric cancer, pancreatic cancer, bone cancer, ovarian cancer, uterine cancer, cervical cancer, testicular cancer, bladder cancer, renal cancer, thyroid cancer, and leukemia. For example, the cancer can be a lung cancer, colorectal cancer, pancreatic cancer, ovarian cancer, or a thyroid cancer. The lung cancer can be an adenocarcinoma, a squamous cell carcinoma, large cell carcinoma, or a small cell carcinoma. The lung cancer can also be a mesothelioma.

The blood sample can be, for example, whole blood, plasma, or serum. A blood sample can be obtained by peripheral vein puncture (venipuncture) or other methods known in the art. The blood sample can be obtained from a subject with cancer, or alternatively, from a subject at risk of developing cancer. For example, the subject can be at risk of developing lung cancer. Risks associated with lung cancer include smoking exposure to asbestos, personal or family history of lung cancer, or sustained passive exposure to smoke.

Optionally, the cancer is stage 0, stage I, stage II, stage Ill, or stage IV cancer. Classifying a cancer by stage uses numerals 0, 1, II, III, and IV to describe the progression of cancer. The stage of a cancer indicates how much the cancer has spread and may take into account size and metastasis of the tumor to distant organs. Stages 0, I, and II cancers are considered early stage tumors. Stages III and IV are considered late stage cancers. Stage 0 indicates carcinoma in situ, i.e., an early form of a carcinoma defined by the absence of invasion of surrounding tissues. Stage I cancers are localized to one part of the body. Stage II cancers are locally advanced, as are stage III cancers. Whether a cancer is designated as stage II or stage II therefore differs according to diagnosis. Stage IV cancers have metastasized or spread to other organs or throughout the body. The provided methods can be used to diagnose early stage cancers (stages 0, I, and II) as well as late stage (stages III and IV) cancers.

The provided methods can also be used to differentiate early stage (stage 0, I, or II) from late stage (Ill or IV) cancer, or to monitor cancer progression. Specifically, blood levels of Ca-1 and/or Ca-2 increases in some late stage cancers as compared to early stage or control. Therefore, blood levels of eCa-1 and/or Ca-2 in some 0, I, and II stage cancers is lower than the blood level of Ca-1 and/or Ca-2 in the corresponding stage III or IV cancers. Blood levels of eCa-1 and/or Ca-2 can increase in certain cancers with increased metastasis or with an increased tumor size. Thus, provided are methods of determining a stage of progression of a cancer in a subject. The methods comprise selecting a subject with cancer, obtaining a blood sample from the subject, and determining a blood level of Ca-1 and/or Ca-2 isoforms, or a calculated value thereof, in the sample. The blood level of Ca-1 and/or Ca-2 isoforms can be compared to a known value or reference sample or with a previous blood sample from the subject.

The blood level of Ca-1 and/or Ca-2 isoforms or a calculated value thereof can, for example, be compared to a previous blood sample from the subject. A previous blood sample can be a sample from the same subject isolated at a time prior to the isolation of the most recent blood sample. A higher level of expression as compared to a previous blood sample indicates progression or metastasis of the cancer. Progression or metastasis generally indicates the need for additional testing, a change in treatment dosage or frequency, or a more aggressive treatment (i.e., a new treatment agent). A lower level of expression as compared to previous blood sample indicates improvement in the cancer. Generally, such an improvement indicates the success of the treatment. In such case, the treatment can be continued or even discontinued if the level or calculated value thereof for Ca-1 and/or Ca-2 isoforms is sufficiently low.

The blood level of Ca-1 and/or Ca-2 isoforms or calculated value thereof can, for example, be compared to a known value or a reference sample(s). A lower blood level of Ca-1 and/or Ca-2 isoforms or calculated value thereof as compared to a known value or a reference sample for a stage III or IV cancer can indicate the subject has stage 0, I, or II cancer. A higher level of Ca-1 and/or Ca-2 isoforms or calculated value thereof as compared to a known value or a reference sample for a stage 0, I, or II cancer can indicate the subject has stage III or IV cancer. Comparable levels of Ca-1 and/or Ca-2 isoforms or calculated value thereof to a known value or reference sample for a stage 0, I, II, III, or IV cancer can indicate the subject has a stage 0, I, II, III, or IV cancer, respectively.

As used herein, a known value refers to a value (e.g., blood level of Ca-1 and/or Ca-2 isoforms) obtained from a nondiseased sample, a diseased sample, or a group of samples, which can represent, for example, an untreated sample, a sample from the same subject at various stages and/or treatment conditions, or a sample from a different subject (treated or untreated). A known value can, for example, be a value obtained from a blood sample from the same subject prior to the treatment of the cancer, wherein the cancer has been assigned a designated stage (e.g., a stage I cancer). A known value can, for example, be a value obtained from a blood sample from the same subject after treatment of the cancer. A reference sample can, for example, include an untreated subject with stage 0, I, II, III, or IV cancer. By way of another example, a reference sample can include a treated subject with stage 0, I, II, III, or IV cancer. By way of another example, a reference sample can be the baseline level of expression in a subject with a stage 0, I, II, III, or IV cancer. Reference samples or value can include a known value or can be positive or negative control samples (optionally, matched for age, stage of cancer, or type of cancer with the experimental sample(s)) run in parallel with the experimental sample.

Ca-1 and/or Ca-2 isoform levels are in some cases higher in younger subjects than in older subjects. Therefore, in some cases, the subject of the disclosed methods is at least 35, 40, 45, 50, or 55 years of age. Optionally, the blood level of Ca-1 and/or Ca-2 isoforms and positive and negative control values are normalized for the age of the subject.

Also provided is a method of determining efficacy of a cancer therapy in a subject based on a change or changes in the Ca-1 and/or Ca-2 blood levels or calculated value thereof. The method comprises obtaining a first blood sample from a subject with cancer prior to treatment with a first cancer therapy, determining a first Ca-1 and/or Ca-2 value in the first blood sample (i.e., as a baseline measurement), obtaining a second blood sample from a subject with cancer after at least one treatment with the first cancer therapy, determining a second Ca-1 and/or Ca-2 value in the second blood sample (i.e., as a means of assessing the treatment effect), and comparing the first value to the second value. In this method, a decrease in Ca-1 and/or Ca-2 from the first to the second blood sample is an indication of effective cancer therapy that can be continued, e.g., until blood levels reach negative control levels or reduced to a maintenance dosing regimen. However, minimal decrease or an increase in Ca-1 and/or Ca-2 isoform levels from the first to the second blood sample is an indication that the cancer therapy is insufficiently effective and that a second cancer therapy or an increase in dosing regimen (increased dosage or frequency using the current treatment agent) for the subject should be selected. A second cancer therapy can also include administration of multiple chemotherapeutics in combination, surgery, and/or radiation therapy. One of skill in the art can determine the proper dosages or change in treatment regimen.

BIN1 isoforms without the polypeptide encoded by exon 12a function as tumor suppressors, and this activity may be related to the suppression of indoleamine 2,3-dioxygenase (IDO) (Muller A J, et al., *Nature Medicine* 2005 11(3):312-319). IDO has been shown to be active in particular forms of cancer, including lung cancer (Smith C, et al., *Cancer Discovery* 2012 2(8):723-735). Cancer therapeutics are being developed that mimic BIN1 suppression of IDO (Novitskiy S V and Moses H L. *Cancer Discovery* 2012 2(8):673-5). The disclosed methods may therefore by used to detect the physiological state in which IDO is active. Because IDO blocking agents are being developed as cancer therapeutics, the disclosed methods may be used to identify that particular subset of cancer patients who will respond to IDO blocking therapeutics. Among the current clinical trials registered using IDO antagonists, lung cancer is being targeted, and a significant portion of lung cancers are shown herein to have a high blood levels of BIN1 cancer isoform signal.

Therefore, also provided are methods of treating cancer in a subject that comprise administering an inhibitor of IDO to the subject having an elevated Ca-1 and/or Ca-2 value. The method involves obtaining a blood sample from the subject, determining a blood level of Ca-1 and/or Ca-2 isoforms or a calculated value thereof, and comparing these levels to one or more control levels or values. In these methods, determination of elevated blood levels of Ca-1 and/or Ca-2 isoforms or a calculated value thereof is an indication that the subject has a subset of cancers that should be treated with an inhibitor of IDO. Examples of IDO inhibitors include 1-methyl-tryptophan (1-MT), 1-methyl-D-tryptophan, and INCB024360 (InCyte, Wilmington, Del.).

Ca-1 and/or Ca-2 may also be a more specific marker in disease states that correspond to an elevated blood level of IDO such as tuberculosis. Therefore, also disclosed are methods of using Ca-1 and/or Ca-2 as a diagnostic and as an assay for evaluating the treatment effectiveness of IDO-related diseases.

Also provided are methods of detecting the recurrence of cancer in a subject. The methods comprise selecting a subject with a cancer in remission, obtaining a blood sample from the subject, and determining a level of Ca-1 and/or Ca-2 isoforms or a calculated value thereof in the blood sample. An elevated level of Ca-1 and/or Ca-2 isoforms or calculated value thereof as compared to a negative control level or value indicates that the subject has a recurrence of cancer or is at risk for a recurrence of cancer. If recurrence or the risk of recurrence is detected, additional tests or therapy can be performed. Such tests and therapy are described herein and are within the skill in the art.

The level of Ca-1 and/or Ca-2 isoforms can, for example, be determined by detecting 12a+ BIN1 polypeptide in the biological sample. Optionally, the level of 12a+ BIN1 polypeptide is determined using an antibody that is specific for the polypeptide encoded by exon 12a of BIN1 (12a+ BIN1) specific antibody. For example, the antibody can optionally selectively bind SEQ ID NO:1 (polypeptide encoded by exon 12a) but does not bind isoform 2, which lacks exon 12a. Human BIN1 isoform 2 can have the following amino acid sequence:

```
                (SEQ ID NO: 3, Accession No. NP_647594.1)
MAEMGSKGVT AGKIASNVQK KLTRAQEKVL QKLGKADETK

DEQFEQCVQN FNKQLTEGTR LQKDLRTYLA SVKAMHEASK

KLNECLQEVY EPDWPGRDEA NKIAENNDLL WMDYHQKLVD

QALLTMDTYL GQFPDIKSRI AKRGRKLVDY DSARHHYESL

QTAKKKDEAK IAKPVSLLEK AAPQWCQGKL QAHLVAQTNL

LRNQAEEELI KAQKVFEEMN VDLQEELPSL WNSRVGFYVN

TFQSIAGLEE NFHKEMSKLN QNLNDVLVGL EKQHGSNTFT

VKAQPSDNAP AKGNKSPSPP DGSPAATPEI RVNHEPEPAG

GATPGATLPK SPSQFEAPGP FSEQASLLDL DFDPLPPVTS

PVKAPTPSGQ SIPWDLWEPT ESPAGSLPSG EPSAAEGTFA

VSWPSQTAEP GPAQPAEASE

VAGGTQPAAG AQEPGETAAS EAASSSLPAV VVETFPATVN

GTVEGGSGAG RLDLPPGFMF KVQAQHDYTA TDTDELQLKA

GDVVLVIPFQ NPEEQDEGWL MGVKESDWNQ HKELEKCRGV

FPENFTERVP.
```

Therefore, an isolated antibody is disclosed that can selectively bind SEQ ID NO:1 but not bind SEQ ID NO:3. The antibody can be a monoclonal antibody or a recombinant antibody. A monoclonal antibody (9D7 1C1) that specifically binds exon 12a is disclosed and described in Example 3. The complementarity determining regions (CDRs) of the 9D7 1C1 antibody's heavy chain comprises the amino acid sequences SEQ ID NO:10, SEQ ID NO: 11, and SEQ ID NO:12. The CDRs of the 9D7 1C1 antibody's light chain comprise the amino acid sequences SEQ ID NO: 13, SEQ ID NO: 14, and SEQ ID NO: 15. Therefore, the disclosed monoclonal or recombinant antibody that selectively binds the 12a+ BIN1 polypeptide comprises at least these CDRs, or CDRs having at least 95% to 99% identity with SEQ ID NO:10, SEQ ID NO: 11, SEQ ID NO:12, SEQ ID NO:13, SEQ ID NO:14, and SEQ ID NO:15.

Examples of analytical techniques useful in determining the expression of 12a+ BIN1 polypeptide include immunohistochemistry, Western blot, enzyme-linked immunosorbent assay (ELISA), enzyme immunoassay (EIA), radioimmunoassay (RIA), protein array, or fluorescent activated cell sorting (FACS). Using a specific antibody against exon 12a BIN1 polypeptide, FACS can be used to detect cells expressing exon 12a+ BIN1 circulating in blood and/or microparticles and/or tumor cells and/or apoptotic cell fragments expressing 12a+ BIN1 circulating in plasma or serum. These techniques are known by one of skill in the art. See, e.g., Sambrook et al., Molecular Cloning: A Laboratory Manual, $3^{rd}$ Ed., Cold Spring Harbor Press, Cold Spring Harbor, N.Y. (2001).

Immunohistochemical methods may also be used for detecting the expression levels of 12a+ BIN1 polypeptide. Thus, antibodies or antisera, such as, polyclonal antisera and monoclonal antibodies specific for 12a+ BIN1 polypeptides may be used to assess 12a+ BIN1 polypeptide expression. The antibodies can be detected by direct labeling of the BIN1 antibodies themselves, for example, with radioactive labels, fluorescent labels, hapten labels such as biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody that binds the primary antibody. Labeled tertiary antibodies can be used similarly. Optionally, 12a+ BIN1 polypeptide expression in a blood sample from a patient may be compared to 12a+ BIN1 expression in a blood sample of a normal subject or the same subject before or after cancer.

In certain cases, the level of 12a+ BIN1 isoforms present in a blood sample may be determined by a Western blot. For example, polypeptides present in the whole cell lysate from a blood sample may be separated by SDS-PAGE; the separated polypeptides transferred to a nitrocellulose membrane: 12a+ BIN1 polypeptide detected by using an antibody or antiserum specific for BIN1 or a specific isoform of 12a+ BIN1. At least one normalizing polypeptide, for example, CaV 1.2 or a housekeeping polypeptide such as GAPDH can be detected simultaneously or in parallel and used to normalize the BIN polypeptide expression levels. BIN1 expression level may be determined by performing a BIN1 immunoprecipitation using an excess of anti-BIN1 antibody (e.g., an antibody specific for 12a+ BIN1 polypeptide). The immunoprecipitation is followed by separation of the immunoprecipitate by SDS-PAGE; the separated polypeptides are transferred to a nitrocellulose membrane; and detected by staining the gel. e.g., by Coomassic Blue or silver staining. Immunoprecipitation of a control protein such as GAPDH or ubiquitin may also be carried out either simultaneously or in parallel. Optionally, the same procedure may be carried out on corresponding normal tissue or from a sample from a normal subject.

In certain cases, the level of 12a+ BIN1 isoforms in cells or microparticles within human blood can be determined by FACS analysis. FACS is an established method used to detect cells as well as circulating microparticles. Microparticle analysis by FACS has been successfully used for thrombotic disease diagnosis and prognosis. In cancer, in particular metastasized cancer, tumor cells expressing 12a+ BIN1 can be potentially released into circulation. These cells may release microparticles carrying 12a+ BIN1. Human blood samples can be fixed in paraformaldehyde (PFA) followed by labeling the cells and/or microparticles with antibody specifically against 12a+ BIN1 polypeptide. The antibodies can be detected by direct labeling of the BIN1 antibodies with fluorescent labels or unlabeled primary antibody used in conjunction with a labeled secondary antibody, comprising antisera, polyclonal antisera, or a monoclonal antibody specific for the primary antibody. Fluorescently labeled 12a+ BIN1 positive cells and/or microparticles can be sorted out by FACS analysis. Optionally, 12a+ BIN1 polypeptide expression in a blood sample from a patient may be compared to 12a+ BIN1 polypeptide expression in a blood sample in a normal subject or the same subject before or after cancer. Similarly, a mobile solid support like fluorescent beads with bound antibody (e.g., antibody selective for 12a+ BIN1) can be used in FACS analysis, wherein beads of differing fluorescence are used to correlate with different bound antibodies.

Optionally, the level of 12a+ BIN1 expression can be determined by detecting a BIN1 nucleic acid comprising exon 12a (e.g., exon 12a+ BIN1 mRNA), or fragment thereof, in the sample. Examples of analytical techniques useful in determining the expression of exon 12a+ BIN1 mRNA include reverse transcription-polymerase chain reaction (RT-PCR), quantitative real time-PCR (qRT-PCR), one step PCR, RNase protection assay, primer extension assay, microarray analysis, gene chip, in situ hybridization, and Northern blot.

When RT-PCR is used to determine exon 12a+ BIN1 mRNA expression, mRNA can be isolated from the sample. Optionally, RNA is isolated from blood or plasma of the subject. Normal blood or plasma of another subject can be a control. A normal blood or plasma sample from the same subject before cancer or after cancer is successfully treated can be a control.

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). Optionally, RNA isolation can be performed using a purification kit, buffer set and protease from commercial manufacturers according to the manufacturer's instructions. For example, total RNA can be isolated using Qiagen RNeasy® mini-columns (Hilden, Del.). Other commercially available RNA isolation kits include MasterPure® Complete DNA and RNA Purification Kit (EPICENTRE®, Madison, Wis.), and Paraffin Block RNA Isolation Kit® (Ambion, Inc., Austin, Tex.). Total RNA from tissue samples can be isolated using RNA Stat-60® (Tel-Test, Friendswood, Tex.). RNA prepared from a biological sample can be isolated, for example, by cesium chloride density gradient centrifugation.

The RNA template can be transcribed into cDNA, followed by its exponential amplification in a PCR reaction. One or more of a number of reverse transcriptases may be used, including, but not limited to, Avian Myeloblastosis Virus Reverse Transcriptase (AMV-RT), Moloney Murine Leukemia Virus Reverse Transcriptase (MMLV-RT), reverse transcriptase from human T-cell leukemia virus type I (HTLV-I), bovine leukemia virus (BLV), Rous sarcoma virus (RSV), human immunodeficiency virus (HIV) and Thermus thermophilus (Tth). The reverse transcription step is typically primed using specific primers, random hexamers, or oligo-dT primers, depending on the circumstances and the goal of RT-PCR. For example, extracted RNA can be reverse-transcribed using a GeneAmp RNA PCR kit (Perkin Elmer; Waltham, Mass.), following the manufacturer's instructions. The derived cDNA can then be used as a template in the subsequent PCR reaction.

Although the PCR step can use a variety of thermostable DNA-dependent DNA polymerases, typically employed is the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

RT-PCR can be performed using commercially available equipment, such as, for example, ABI PRISM 7700™ Sequence Detection System® (Perkin-Elmer-Applied Biosystems; Foster City, Calif.), or Lightcycler® (Roche Molecular Biochemicals; Mannheim, Del.). Optionally, the 5' nuclease procedure is run on a real-time quantitative PCR device. Such a system can comprise a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as a threshold cycle (Ct). Fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is optionally performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A variation of the RT-PCR technique is the real time quantitative PCR, which measures PCR product accumulation through a dual-labeled fluorogenic probe. Real time PCR is compatible both with quantitative competitive PCR, where internal competitor for each target sequence is used for normalization, and with quantitative comparative PCR using a normalization gene contained within the sample, or a housekeeping gene for RT-PCR.

To correct for (normalize away) both differences in the amount of RNA assayed and variability in the quality of the RNA used the assay can optionally incorporate analysis of the expression of certain reference genes (or "normalizing genes"), including well known housekeeping genes, such as GAPDH, HPRT1, ubiquitin, etc.

Alternatively, normalization can be based on the mean or median signal of all of the assayed genes or a large subset thereof (often referred to as a "global normalization" approach). On a gene-by-gene basis, measured normalized amount of a subject tissue mRNA may be compared to the amount found in a corresponding normal tissue.

For example, primers and probes (e.g., for use in PCR amplification-based methods) can be designed based upon an exon sequence to be amplified. Accordingly, the primer/probe design can include determining a target exon sequence within the gene of interest (e.g., exon 12a of BIN1). This can be done by publicly available software, such as the DNA BLAST software developed by Kent, W. J., Genome Res. 12(4):656-64 (2002), or by the BLAST software including its variations. Subsequent steps follow well established methods of PCR primer and probe design.

In order to avoid non-specific signals, repetitive sequences within the target sequence of the gene can be optionally masked when designing the primers and probes. The masked sequences can then be used to design primer and probe sequences using any commercially or otherwise publicly available primer/probe design packages, such as Primer Express (Applied Biosystems; Carlsbad, Calif.): MGB assay-by-design (Applied Biosystems; Carlsbad, Calif.).

Factors to be considered in PCR primer design can include primer length, melting temperature (Tm), G/C content, specificity, complementary primer sequences, and 3'-end sequence. PCR primers can optionally be 17-30 bases in length, and contain about 20-80% G+C bases, (e.g., about 50-60% G+C bases). Tms are between 50° C. and 80° C., e.g. about 50° C. to 65° C.

Microarray technology may be used to detect differential expression of exon 12a+ BIN1 in a subject's blood sample and normal or control blood sample. In this method, polynucleotide sequences of interest (including cDNAs and oligonucleotides) are plated, or arrayed, on a microchip substrate. The arrayed sequences are then hybridized with specific DNA probes from blood samples of interest. Similar to the RT-PCR method, the source of mRNA is optionally total RNA isolated from subject's blood sample, and optionally corresponding normal or control blood sample.

Fluorescently labeled cDNA probes can be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element can be used for assessment of corresponding mRNA abundance.

With dual color fluorescence, separately labeled cDNA probes generated from two sources of RNA are hybridized pair wise to the array. The relative abundance of the transcripts from the two sources corresponding to each specified gene is thus determined simultaneously. Microarray methods have been shown to have the sensitivity to detect rare transcripts, which are expressed at a few copies per cell, and to reproducibly detect at least approximately two-fold differences in the expression levels (Schena et al., Proc. Natl. Acad. Sci. USA 93(2):106-149 (1996)).

The arrayed oligonucleotides may include oligonucleotides which hybridize to a specific region of the exon 12a+ BIN1 nucleic acid. In certain embodiments, multiple copies of a first oligonucleotide which specifically hybridizes to a first region of the exon 12a+ BIN1 nucleic acid are arrayed. In certain embodiments, multiple copies of first and a second oligonucleotide which specifically hybridize to a first and a second region of the exon 12a+ BIN1 nucleic acid, respectively, are arrayed, and so on. In certain embodiments, the exon 12a+ BIN1 nucleic acid expression level is determined by mean values of the signal from each of these oligonucleotides. The array may also include oligonucleotides which specifically hybridize to nucleic acid of a normalizing gene, such as a housekeeping gene or other genes known not to be significantly differentially expressed in diseased versus normal tissue, for example, CaV 1.2.

Optionally, the BIN1 polypeptide, nucleic acid, or fragments of said polypeptides or nucleic acids detected is human. Optionally, BIN1 polypeptide, nucleic acid, or fragments of said polypeptides or nucleic acids detected is non-human mammal (e.g., rodent, porcine, bovine, equine, canine, or feline).

There are a variety of BIN1 sequences that are disclosed on Genbank, and these sequences and others are herein incorporated by reference in their entireties as are individual subsequences or fragments contained therein. As used herein, BIN1 includes homologs, variants, and isoforms thereof.

The nucleotide and amino acid sequences of BIN1 isoforms 1-10 can be found at GenBank Accession Nos. NM_139343.2 and NP_647593.1 for isoform 1; NM_139344.2 and NP_647594.1 for isoform 2; NM_139345.2 and NP_647595.1 for isoform 3; NM_139346.2 and NP_647596.1 for isoform 4; NM_139347.2 and NP_647597.1 for isoform 5; NM_139348.2 and NP_647598.1 for isoform 6; NM_139349.2 and NP_647599.1 for isoform 7; NM_004305.3 and NP_04296.1 for isoform 8; NM_139350.2 and NP_647600.1 for isoform 9; and NM_139351.2 and NP_647601.1 for isoform 10. Two other reported exon 12a+ BIN1 tumor isoforms include BIN1+12a found at GenBank Accession Nos. AF068918.1 and AAC23751.1 for nucleotide and amino acid sequences, respectively, and BIN1-10+12a found at GenBank Accession Nos. AF068917.1 and AAC23750.1 for nucleotide and amino acid sequence, respectively. The nucleotide and amino acid sequence of exon 12a is given by SEQ ID NO:2 and SEQ ID NO:1, respectively.

Thus, provided are the nucleotide sequences of BIN1 comprising exon 12a+(SEQ ID NO:2) comprising a nucleotide sequence at least about 70%, 75%, 80%/o, 85%, 90%, 95%, 98%, 99% or more identical to the nucleotide sequences of the aforementioned GenBank Accession Numbers. Also provided are amino acid sequences of the BIN1 polypeptide comprising the encoded amino acid sequence of exon 12a+(SEQ ID NO:1) comprising an amino acid sequence at least about 70%, 75%, 80%, 85%, 90%, 95%, 98%, 99% or more identical to the sequences of the aforementioned GenBank Accession Numbers.

Antibodies that bind the polypeptides described above, including 12a+ BIN1, or polypeptide fragments thereof, can be used to detected 12a+ BIN1 isoforms in a biological sample. For example, the polypeptides described above can be used to produce antibodies to 12a+ BIN1.

As used herein, the term antibody encompasses, but is not limited to, whole immunoglobulin (i.e., an intact antibody) of any class. Chimeric antibodies and hybrid antibodies, with dual or multiple antigen or epitope specificities, and fragments, such as F(ab')2, Fab', Fab and the like, including hybrid fragments are useful herein. Thus, fragments of the antibodies that retain the ability to bind their specific antigens are provided and are useful in the methods taught here. For example, fragments of antibodies which maintain binding activity to 12a+ BIN1 expressed in cancers are included within the meaning of the term antibody or fragment thereof. Such antibodies and fragments can be made by techniques known in the art and can be screened for specificity and activity according to general methods for producing antibodies and screening antibodies for specificity and activity (See Harlow and Lane. Antibodies, A Laboratory Manual. Cold Spring Harbor Publications, New York (1988)).

Also useful in the methods herein are conjugates of antibody fragments and antigen binding proteins (single chain antibodies) as described, for example, in U.S. Pat. No. 4,704,692, the contents of which are hereby incorporated by reference in their entirety.

Optionally, the antibody is a monoclonal antibody. The term monoclonal antibody as used herein refers to an antibody from a substantially homogeneous population of antibodies, i.e., the individual antibodies comprising the population are identical except for possible naturally occurring mutations that may be present in minor amounts. Monoclonal antibodies may be prepared using hybridoma methods, such as those described by Kohler and Milstein, Nature, 256:495 (1975) or Harlow and Lane, Antibodies, A Laboratory Manual. Cold Spring Harbor Publications, New York (1988). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro. The immunizing agent can be 12a+ BIN1 expressed in cancer or an immunogenic fragment thereof.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The DNA also may be modified, for example, by substituting the coding sequence for human heavy and light chain constant domains in place of the homologous murine sequences or by covalently joining to the immunoglobulin coding sequence all or part of the coding sequence for a non-immunoglobulin polypeptide. Such a non-immunoglobulin polypeptide can be substituted for the constant domains of an antibody provided herein, or can be substituted for the variable domains of one antigen-combining site of an antibody to create a chimeric bivalent antibody comprising one antigen-combining site having specificity for 12a+ BIN1 expressed in cancer and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment that has two antigen combining sites and is still capable of cross-linking antigen.

The Fab fragments produced in the antibody digestion can also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group.

Further provided herein is a humanized or human version of the antibody. Humanized and human antibodies can be made using methods known to a skilled artesian; for example, the human antibody can be produced using a germ-line mutant animal or by a phage display library.

Antibodies can also be generated in other species and humanized for administration to humans. Alternatively, fully human antibodies can also be made by immunizing a mouse or other species capable of making a fully human antibody (e.g., mice genetically modified to produce human antibodies) and screening clones that bind exon 12a+ BIN1 expressed in cancer. See, e.g., Lonberg and Huszar, Int. Rev. Immunol. 13:65-93, (1995), which is incorporated herein by reference in its entirety for methods of producing fully human antibodies. As used herein, the term humanized and human in relation to antibodies, relate to any antibody which is expected to elicit a therapeutically tolerable weak immunogenic response in a human subject. Thus, the terms include fully humanized or fully human as well as partially humanized or partially human.

Kits containing one or more of the disclosed antibodies are also provided for detecting Ca-1 and/or Ca-2 isoform levels. The kit can contain an assay system for detecting 12a+ BIN1 polypeptides and an assay system for detecting 12a+/13+ BIN1 polypeptides. For example, the kit can contain a first assay system for detecting 12a+ BIN1 isoforms that comprises an antibody that selectively binds 12a+ BIN1, and an antibody that selectively binds multiple human BIN1 isoforms. The assay may also be a sandwich assay, wherein one of these two antibodies is immobilized on a solid surface. The kit can contain a second assay system for detecting 12a+/13+ BIN polypeptides that comprises an antibody that selectively binds 13+ BIN1, and an antibody that selectively binds 12a+ of BIN1. The assay may also be a sandwich assay, wherein one of these two antibodies is immobilized on a solid surface. The solid support can include a plate, array, chip or bead. Optionally the antibodies of the kit are labeled. The kit optionally includes one or more secondary and/or tertiary antibodies (optionally labeled), containers for the antibodies, and/or regents for detection of the labels. The assay system optionally includes one or more solid supports with the selected antibody or antibodies bound thereto.

As used throughout, subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g., cancer). The term patient or subject includes human and veterinary subjects.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 700%, 80%, 90%, 100%, or any percent reduction in between 10% and 100%/s as compared to native or control levels. It is understood that treatment does not necessarily refer to a cure or complete ablation of the disease, condition, or symptoms of the disease or condition.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods of using the disclosed compositions. Thus, if there are a variety of additional steps that can be performed it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1: Canine Study of BIN1 in Blood Samples

Methods

Canine Selection and Serum Acquisition.

Venous blood samples were obtained from 31 dogs with a definite diagnosis of carcinoma and seven healthy dogs as controls. Two samples were excluded due to high muscle contaminant (creatinine kinase >1000 IU/L) and another two samples were excluded due to incomplete clinical data. The remaining 27 samples had their cancer staged (l-IV), according to standardized clinical (not biopsy based) staging guidelines for each respective cancer. The cancers were a mix between solid and blood-based tumors, including lymphoma, sarcoma, adenosarcoma, and undifferentiated tumor.

Each dog was restrained in a sternal recumbancy. 5 mls of venous blood was collected into a 7.0 ml glass EDTA tube from the jugular vein using a 12.0 ml syringe with a 21 gauge-1 inch needle. After mixed with EDTA, the blood was then centrifuged at 4,000 rpm for 20 minutes at 4° C. The supernatant serum was collected into a 1.7 ml Eppendorf tube and stored in −80° C. freezer for later analysis.

Detection of Serum BIN1 Protein by Capture ELISA.

Round bottomed 96-well plates were coated at 4° C. for 16 hours with mouse anti BIN1 (clone 99D, Sigma, 1/1000) (Sigma; St. Louis, Mo.) diluted in 0.1 M sodium carbonate buffer, pH 9.0. The plates were washed three times with tris-buffered saline tween-20™ (TBST) to remove unbound antibody and blocked for 1 hour at room temperature with 1% bovine serum albumin (BSA) in TBST (blocking buffer). 100 µl of each serum sample was added, in duplicate, and plates were incubated overnight at 4° C. with orbital rotation. The samples were then aspirated and plates were washed twice quickly, followed by three times for 5 minutes with TBST. Goat anti-BIN1 (1/1000 in blocking buffer) (Everest Biotech; Oxfordshire, United Kingdom) was then applied as a detection antibody, and the plates were incubated for 2 hours at room temperature with rotation. The detection antibody was then aspirated and the plates were washed twice quickly, followed by three times for 5 minutes with TBST. The plates were subsequently incubated for 1 hour at room temperature with HRP-conjugated donkey anti-goat IgG (1/2000 in blocking buffer) (Abcam; Cambridge, Mass.) before two quick washes and three 5 minute washes with TBST. TMB substrate was added and plates were incubated in the dark for 1 hour before reaction termination with 1 N hydrochloric acid (HCL). Following the reaction termination, the plates were read using the ELx800 BioTek microplate spectrophotometer (BioTek; Winooski, Vt.), and OD values were determined at 405 nm. All values were normalized to that of a two year old, 9 kilogram healthy dog.

Results

A canine study was undertaken to determine the correlation between serum BIN1 levels and clinically assessed cancer stage. For this study, twenty-seven dogs with a definite diagnosis of carcinoma were studied. Serum was obtained from the animals, and assayed for BIN1 content by ELISA. The capture antibody in the ELISA test was a commercially available monoclonal BIN1 antibody against the region encoded by BIN1 exon 13 (clone 99D, sigma). As indicated in FIG. 1, dogs with limited cancer (Stage I) has significantly less serum BIN1 that dogs with advanced cancer (Stage III and IV). Of note, the dogs in this cohort did not differ significantly between weight, age, or creatinine phospho-kinase (indication of muscle sampling).

This proof of principle study is supportive of BIN1 as a blood available cancer diagnostic tool. Elevation of BIN1 in the serum fraction of venous blood significantly predicts stage III or IV status of carcinoma in canines. BIN1 could be a quantitative blood biomarker of metastatic cancer in human.

Example 2: Sequence Analysis of 9D7 1C1 Monoclonal Antibody

Materials and Methods

Total RNA Extraction.

Total RNA was extracted from hybridomas using Qiagen kit.

First-Round RT-PCR.

QIAGEN®, OneStep RT-PCR Kit (Cat No. 210210) was used. RT-PCR was performed with primer sets specific for the heavy and light chains. For each RNA sample, 12 individual heavy chain and 11 light chain RT-PCR reactions were set up using degenerate forward primer mixtures covering the leader sequences of variable regions. Reverse primers are located in the constant regions of heavy and light chains. No restriction sites were engineered into the primers. The reaction setup contained 5.0 μl 5× QIAGEN OneStep RT-PCR Buffer, 0.8 μl dNTP Mix (containing 10 mM of each dNTP), 0.5 μl Primer set, 0.8 μl QIAGEN®, OneStep RT-PCR Enzyme Mix, 2.0 μl Template RNA, and RNase-free water to 20.0 μl. The PCR conditions were 50° C., 30 min, 95° C., 15 min, 20 cycles of (94° C., 25 sec; 54° C., 30 sec; and 72° C., 30 see), followed by a final extension at 72° C., 10 min.

Second-Round Semi-Nested PCR.

The RT-PCR products from the first-round reactions were further amplified in the second-round PCR. 12 individual heavy chain and 11 light chain RT-PCR reactions were set up using semi-nested primer sets specific for antibody variable regions. The reaction setup contained 10 μl 2×PCR mix, 2 μl primer set, and 8 μl of the first round product. The PCR conditions were 95° C., 5 min. 25 cycles of (95° C., 25 sec; 57° C., 30 sec; and 68° C. 30 sec), followed by a final extension at 68° C., 10 min.

After PCR was finished, PCR reaction samples were run onto agarose gel to visualize DNA fragments amplified. The correct antibody variable region DNA fragments should have a size between 400-500 base pair.

PCR positive bands were TOPO cloned. The TOPO clones were PCR-amplified, followed by gel electrophoresis and recovery from agarose gel. Approximately 24 clones were then sequenced, and CDR analysis was performed using these sequence data.

Results

After sequencing cloned DNA fragments, several mouse antibody heavy and light chains were identified. Antibody CDR analysis identified one heavy chain and two light chains. A summary of the sequencing results is shown in Table 2.

TABLE 2

Summary of Antibody Sequence Results

| Type | # | Sequencing result summary |
|---|---|---|
| Heavy chain | H1 | Heavy chain |
| Heavy chain | H8 | Not an antibody gene |
| Heavy chain | H9 | Not an antibody gene |
| Light chain | L2 | Not an antibody gene |
| Light chain | L3 | Not an antibody gene |
| Light chain | L4 | Not an antibody gene |
| Light chain | L5 | Not an antibody gene |
| Light chain | L6 | Light chain |
| Light chain | L7 | Light chain (distinct from L6) |
| | | ---CDR1--> <--CDR2-> <--CDR3-- |
| MHC299H1_1_M13R | | GFNIKDYY...._IDPENGNT.._VRGEDYGGYAMDY |
| MHC299H1_2_M13R | | GFNIKDYY...._IDPENGNT.._VRGEDYGGYAMDY |
| MHC299H1_4_M13R | | GFNIKDYY...._IDPENGNT.._VRGEDYGGYAMDY |
| MHC299H1_5_M13R | | GFNIKDYY...._IDPENGNT.._VRGEDYGGYAMDY |
| MHC299L6_1_M13R | | KSLLHSNGNTY._RMS......._MQHLEFPFT |
| MHC299L6_2_M13R | | KSLLHSNGNTY._RMS......._MQHLEFPFT |
| MHC299L6_3_M13R | | KSLLHSNGNTY._RMS......._MQHLEFPFT |
| MHC299L6_5_M13R | | KSLLHSNGNTY._RMS......._MQHLEFPFT |
| MHC299L7_2_M13R | | QDVSTA......_WAS......._QQHYSTPFT |
| MHC299L7_3_M13R | | QDVSTA......_WAS......._QQHYSTPFT |
| MHC299L7_4_M13R | | QDVSTA......_WAS......._QQHYSTPFT |

The following are the sequences listed in Table 2:
GFNIKDYY (SEQ ID NO:10), IDPENGNT (SEQ ID NO:11), VRGEDYGGYAMDY (SEQ ID NO:12), KSLLHSNGNTY (SEQ ID NO:13), RMS (SEQ ID NO: 17), MQHLEFPFT (SEQ ID NO:14), QDVSTA (SEQ ID NO:15), WAS (SEQ ID NO: 18), and QQHYSTPFT (SEQ ID NO:16).

Variable VH Region Sequences

Amino Acid Sequence in FASTA format (MHC299H1.1\; M13R):

(SEQ ID NO: 4)
EVQLQQSGAELVRPGALVKLSCKAS<u>GFNIKDYY</u>VYWVKQRPEQGLEWIG

W<u>IDPENGNT</u>IYDPEFQAKASITADTSSNTAYLQLSSLTSEGTAVYYC<u>VR</u>

<u>GEDYGGY</u>AMDYWGQGTSVTVSS.

Nucleotide Sequence in FASTA format (MHC299H1.1\; M13R):

(SEQ ID NO: 5)
GAGGTCCAGCTGCAGCAGTCTGGGGCTGAGCTTGTGAGGCCAGGGGCCTT

AGTCAAGTTGTCCTGCAAAGCTTCTGGCTTCAACATTAAAGACTACTATG

TGTATTGGGTGAAGCAGAGGCCTGAACAGGGCCTGGAGTGGATTGGATGG

ATTGATCCTGAGAATGGTAATACTATATATGACCCGGAGTTCCAGGCCAA

GGCCAGTATAACAGCAGACACATCCTCCAACACAGCCTACCTGCAGCTCA

GCAGCCTGACATCTGAGGGCACTGCCGTCTATTACTGTGTTAGAGGGGAG

GATTACGGGGCTATGCTATGGACTACTGGGGTCAAGGAACCCTCAGTCAC

CGTCTCCTCA.

Variable VL Region Sequences

Amino Acid Sequence in FASTA format (MHC299L6.3\; M13R):

(SEQ ID NO: 6)
DIVVTQAAPSVPVTPGESVSISCRSS<u>KSLLHSNGNTY</u>LSWFLQRPGQSPQ

LLIY<u>RMS</u>NLASGVPDRFSGSGSGTAFTLRISRVEAEDVGVYYC<u>MQHLEFP</u>

<u>FT</u>FGSGTKLEIK.

Nucleotide Sequence in FASTA format (MHC299L6.3\; M13R):

(SEQ ID NO: 7)
GATATTGTGGTGACTCAGGCTGCACCCTCTGTACCTGTCACTCCTGGAGA

GTCAGTTTCCATCTCCTGCAGGTCTAGTAAGAGTCTCCTGCATAGTAATG

GCAACACTTACTTGTCTTGGTTCCTGCAGAGGCCAGGCCAGTCTCCTCAG

CTCCTGATTTATCGGATGTCCAACCTTGCCTCAGGAGTCCCAGACAGGTT

CAGTGGCAGTGGGTCAGGCACTGCTTTCACACTGAGAATCAGTAGAGTGG

AGGCTGAGGATGTGGGTGTTTATTACTGTATGCAACATCTAGAATTTCCC

TTCACGTTCGGCTCGGGACAAAGTTGGAAATAAAAC.

Variable VL Region Sequences

Amino Acid Sequence in FASTA format (MHC299L7.2\; M13R):

(SEQ ID NO: 8)
DIVMTQSHKFMSTSVGDRVSITCKAS<u>QDVSTA</u>VAWYQQKPGQSPKLLIY<u>W</u>

<u>AS</u>TRHTGVPDRFTGSGSGTDYTLTISSVQAEDLALYYC<u>QQHYSTPFT</u>FGS

GTKLEIK.

Nucleotide Sequence in FASTA format (MHC299L7.2\; M13R):

(SEQ ID NO: 9)
GACATTGTGATGACCCAGTCTCACAAATTCATGTCCACATCAGTAGGAGA

CAGGGTCAGCATCACCTGCAAGGCCAGTCAGGATGTGAGTACTGCTGTAG

CCTGGTATCAACAAAAACCAGGGCAATCTCCTAAACTACTGATTTACTGG

GCATCCACCCGGCACACTGGAGTCCCTGATCGCTTCACAGGCAGTGGATC

TGGGACAGATTATACTCTCACCATCAGCAGTGTGCAGGCTGAAGACCTGG

CACTTTATTACTGTCAGCAACATTATAGCACTCCATTCACGTTCGGCTCG

GGGACAAAGTTGGAAATAAAAC.

Example 3: BIN1 Detection in Blood Samples from Human Cancer Patients

The Bridging integrator 1 (BIN1) gene encodes several isoforms of a nucleocytoplasmic protein. Twenty exons in the BIN1 gene are alternatively spliced to give rise to at least ten BIN1 isoforms (FIG. 3), with ubiquitous or tissue-specific expression. Two BIN1 isoforms that contain exon 12a have been described as tumor isoforms (Prendergast G C. et al., *Biochim Biophys Acta.* 2009 1795(1):25-36): one includes exon 13 (accession number. AF068917.1) with sequence similarity to reported isoform 6 (NM_139348) and is referred as BIN1 isoform 6 in the literature and BIN1 Ca-1 herein, and the other one does not include exon 13 and is referred as BIN1 Ca-2 herein and represents a new cancer isoform (FIG. 3).

This study aims at characterizing BIN1 cancer isoforms containing exon 12a as circulating cancer biomarkers, by employing combinations of antibodies of different specificities to indirectly measuring the level of these isoforms detectable in blood samples from normal and cancer in humans.

Antibody sandwich assay combinations (Table 3) were designed to detect isoforms that contain polypeptides encoded by both exon 12a and exon 13 (Assay #1) or detect isoforms containing polypeptides encoded by exon 12a and ubiquitously expressed exon 11 (Assay #2) which is designed to capture 12a+ BIN1 with and without exon 13. The existence of 12a+/13− BIN1 was detected in the context of the presence of the proto-oncogene splicing factor SF2/ASF (Karni R, et al., *Nature Struct Mol Biology.* 2007 14(3):185-193). This 12a+/13− BIN1 isoform is referred to herein as Ca-2 (FIG. 3).

Materials and Methods

Antibodies.

To measure the levels of BIN1 cancer isoforms in blood samples, a set of four BIN1 antibodies was used in enzyme-linked immunosorbent assay (ELISA). The detection of all BIN1 isoforms was performed using an anti-BIN1 goat polyclonal antibody from Everest (cat #EB08724), named p11 in this study, which specifically recognizes the polypeptide encoded by exon 11, present in all BIN1 isoforms. The detection of the subset of BIN1 isoforms that contain the polypeptide encoded by exon 13 was performed using an anti-BIN1 mouse monoclonal antibody from Sigma (cat #B9428), named m13 in this study. For the detection of the subset of BIN1 isoforms that contain the polypeptide encoded by exon 12a, two custom-made antibodies were used: an anti-BIN1 rabbit polyclonal antibody (#A5299) named p12a in this study, and an anti-BIN1 mouse monoclonal antibody (#9D71C1), named m12a in this study.

Assays and Tests.

Detection of serum BIN1 protein by capture sandwich ELISA. Antibody combinations are listed in Table 3. Round bottomed 96-well plates were coated at 4° C. for 16 hours with capture antibody (approximately 5 pg/ml) diluted in 0.1 M sodium carbonate buffer, pH 9.0. The plates are washed three times with tris-buffered saline TWEEN-20 (TBST) to remove unbound antibody and blocked for 1 hour at room temperature with 1% bovine serum albumin (BSA) in TBST (blocking buffer). 50 µl of standards (recombinant BIN1 proteins) and each serum sample was added, in duplicate, and plates were incubated overnight at 4° C. with rotation. The samples were then aspirated and plates were washed twice quickly and three times for 5 minutes with TBST. Primary detection antibody (5 µg/ml in blocking buffer) was then applied as a detection antibody, and the plates were incubated for 1 hour at room temperature with rotation. The detection antibody was then aspirated and the plates were washed twice quickly, followed by three times for 5 minutes with TBST. The plates were subsequently incubated for 1 hour at room temperature with HRP-conjugated secondary antibody (1/2000 in blocking buffer) before two quick washes and three 5 minute washes with TBST. 3,3',5,5'-Tetramethylbenzidine (TMB) substrate was added and plates were incubated in the dark for 1 hour before reaction termination with 1 N hydrochloric acid (HCL). Following the reaction termination, the plates were read using an ELx800 microplate spectrophotometer (BIOTEK, Winooski, Vt.) and optical density (OD) values were determined at 405 nm. A standard curve was generated from the OD values of the protein standards of known protein concentration. BIN1 concentrations of each sample were then derived from the standard curve.

Two different combinations of these antibodies were used and defined two distinct assays (Table 3). In Assay #1, m13 was used for capture and p12a was used for detection to measure the levels of four BIN1 isoforms including the cancer isoform Ca-1. In Assay #2, m12 was used for capture and p11 was used for detection to measure the levels of five BIN1 isoforms including the two cancer isoforms Ca-1 and Ca-2.

TABLE 3

BIN1 antibodies used in different assays and BIN1 isoforms detected. (Ca-1 and Ca-2 represent BIN1 cancer isoforms)

|  | Capture | Detection | BIN1 isoforms detected |
| --- | --- | --- | --- |
| Assay #1 | m13 | p12a | 1, 4, 5, Ca-1 |
| Assay #2 | m12a | p11 | 1, 4, 5, Ca-1, Ca-2 |

For Assay #2 the secondary HRP conjugated antibody was donkey anti-goat IgG (Abeam). For Assay #1 the secondary HRP conjugated antibody was goat anti-rabbit IgG (Abcam).

To evaluate the levels of BIN1 new cancer isoform Ca-2, the ratio Assay #2/Assay #1 was used and termed BIN1 Cancer Test #1.

Human Samples.

Commercial vendors with human clinical sample repositories, collected under IRB and including relevant clinical data were identified. Forty-two blood samples were obtained (Conversant, Asterand) from unique, clinically normal subjects ranging from 25 to 79. Fifty human blood samples; ten for each of lung, pancreas, colorectal, ovarian and thyroid cancer, were obtained (Innovative Research and Conversant). The ages of the cancer patients ranged from 18 to 84. Blood samples were obtained from lung cancer patients with stage I and IV disease, from pancreas cancer patients with cancer stage III and IV disease, from colorectal cancer patients with stage II, III and IV disease, and ovarian and thyroid cancer patients with all disease stages (I-IV).

Results

Standard Curves.

Figure 4A:
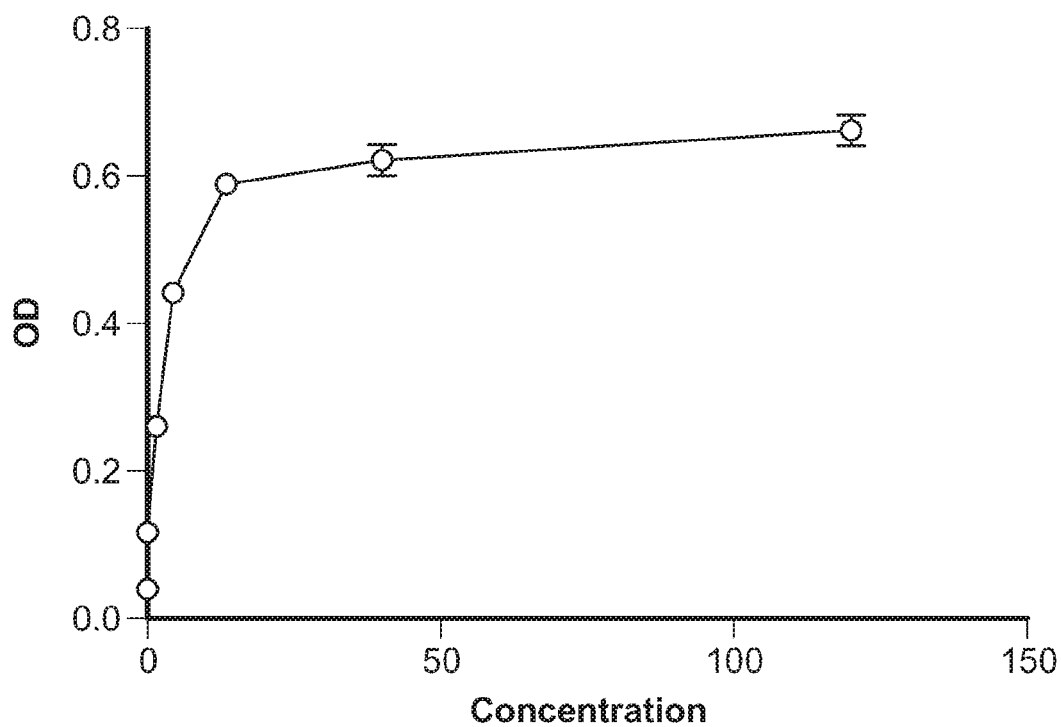
FIGS. 4A and 4B are standard curves of BIN1 recombinant protein using an assay to detect 12a+/13+ BIN1 levels (FIG. 4A) and an assay to detect 12a+ BIN1 (FIG. 4B).
Figure 4B:
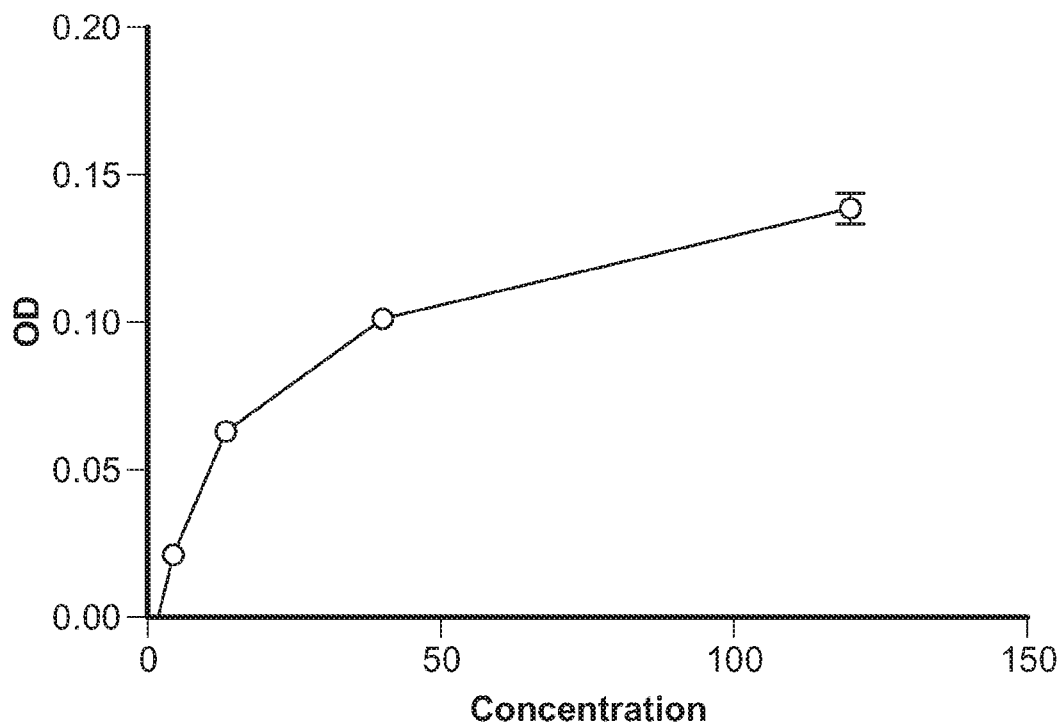

As a positive control for the ELISA assays used in this study, BIN1 recombinant protein (Ca-1) was overexpressed in human HEK-293 cells and the total lysate was analyzed using Assay #1 (m13-p12a) and Assay #2 (m12-p11). The two standard curves for Assay #1 and Assay #2 are represented in FIG. 4A and FIG. 4B, respectively. In both Assay #1 and Assay #2, an increase in the amount of BIN1 recombinant protein correlates with an increase of signal detected using BIN1 antibodies.

Figure 5:
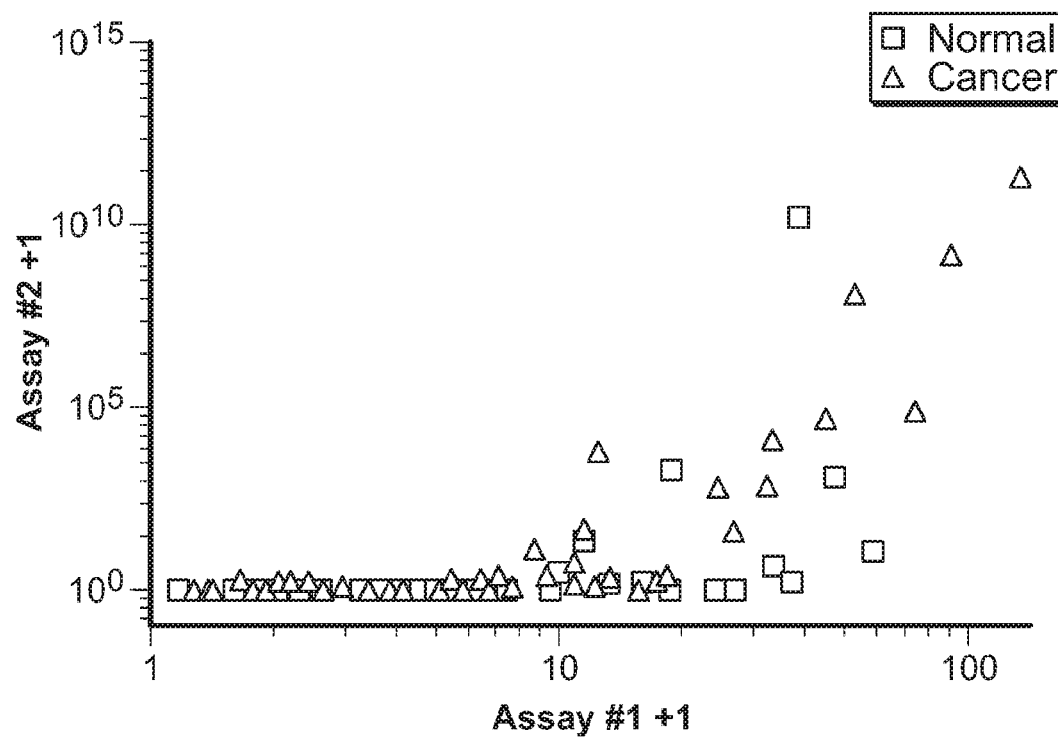
FIG. 5 is a plot showing 12a+/13+ BIN1 levels (x-axis) and 12a+ BIN1 levels (y-axis) in normal (square) and cancer (triangle) samples.

FIG. 5 demonstrates the relationship between the two cancer isoforms, Ca-1 and Ca-2. Many samples give a high signal with Assay #1 (x-axis), both normals and cancer. Combining this with the signal for Assay #2 results in a much better cancer specificity. Ten cancer samples (triangles) with Assay #2 levels above 10 also had Assay #1 levels above 10. As discussed further below, looking at these samples by age is also informative, the higher signal in Normals occurs in samples from younger subjects. This graph demonstrates that both assays show increased signal in cancer, indicating that both Ca-1 and Ca-2 are important. However, samples are analyzed below using a ratio of Assay #2/Assay #1, which allows for determination of Ca-2 cancer isoform levels.

Figure 6:
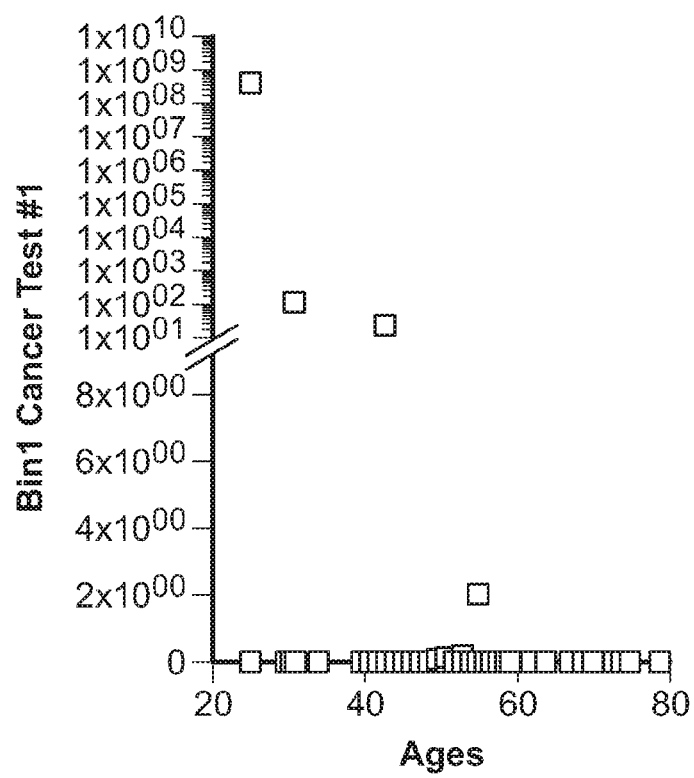
FIG. 6 is a plot showing 12a+/13− BIN1 levels in normal samples as a function of age.

To evaluate the levels of BIN1 cancer isoform Ca-2, BIN1 Cancer Test #1 was used (ratio Assay #2/Assay #1). FIG. 6 shows the BIN1 Cancer Test #1 results, related to subject age in normal blood samples. Three normal samples showed results above 10 (i.e. at the Hatch marks on the y-axis). These samples derive from younger patients between 25 and 43 years old. Nearly all the normal samples have a very low Cancer Test #1 values.

Figure 7:
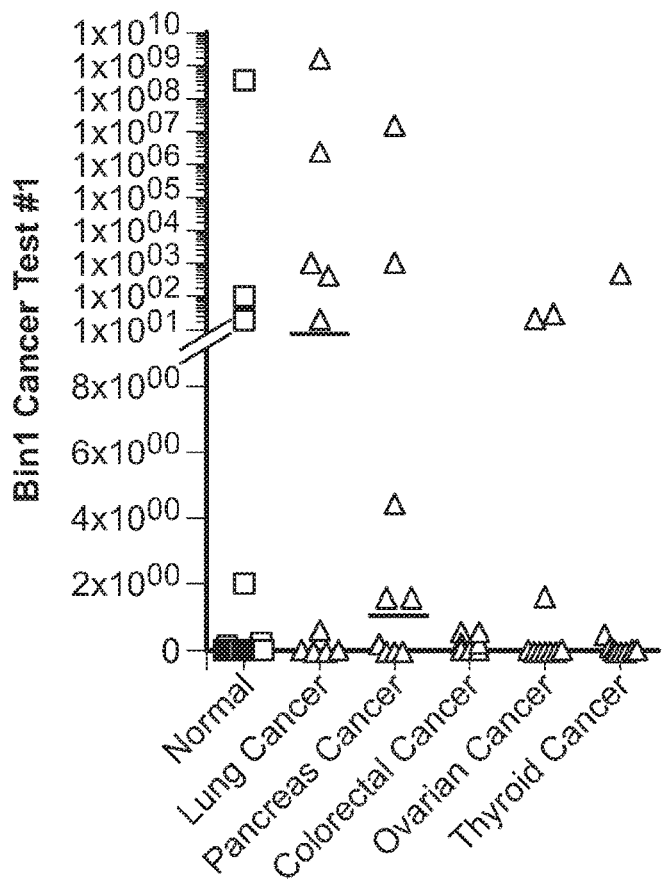
FIG. 7 is a plot showing 12a+/13− BIN1 levels in human normal, lung cancer, pancreatic cancer, colorectal cancer, ovarian cancer, and thyroid cancer samples. Horizontal bars represent the median.

In FIG. 7, the BIN1 Cancer test #1 was used to evaluate the cancer samples and these results are plotted with the results obtained with the normal samples. A test value above of 10 was observed in ten cancer samples including lung, pancreas, ovarian and thyroid cancer. Lung cancer showed the highest levels of Ca-2 (exon 12a+/13−BIN1), both quantitatively and numerically, thus five of ten samples were positive and these were among the highest levels observed. The levels of Ca-2 BIN1 cancer isoform in colorectal cancer were uniformly very low, while a few samples from subjects with each of the other cancer types did show levels above 10; including two pancreas samples, two ovarian samples and one thyroid samples.

The youngest cancer patient with a Test value above 10 in this small survey was 56 years old, whereas among the three normal subjects with elevated BIN1 test values, the oldest is 43 years old. Thus in the age groups in which one is most likely to consider a cancer screening test, the separation of the test results in the cancer samples and normals is very good at a level of 10:20% of cancers are positive, and no normals are positive in persons >50 years old. Half of the lung cancer samples were positive suggesting the use of a BIN1 test to screen smokers, and others with a high risk of lung cancer. Interestingly, three of these lung cancers that were detected were Stage I, thus these patients may gain significant benefit from early detection and directed treatment.

Table 4 summarizes the human clinical results using BIN1 Cancer Test #1 and an increasing threshold of test signal. (* these normals are <=43 years old, ˆ these cancer subjects are >=56 years old).

TABLE 4

Percentage of detection of BIN1 cancer isoform in Normal and Cancer samples.

| BIN1 Cancer Test #1 | % of Normal | % of Cancer |
|---|---|---|
| >1 | 9.5 | 28.0 |
| >10 | 7.1* | 20.0ˆ |
| >100 | 4.8 | 14.0 |
| >1000 | 2.4 | 10.0 |
| >1.00E+04 | 2.4 | 6.0 |
| >1.00E+05 | 2.4 | 6.0 |
| >1.00E+06 | 2.4 | 6.0 |
| >1.00E+07 | 2.4 | 4.0 |
| >1.00E+08 | 2.4 | 2.0 |
| >1.00E+09 | 0.0 | 2.0 |

*these normals are ≤43 years old
ˆthese cancer subjects are ≥56 years old

Figure 8:
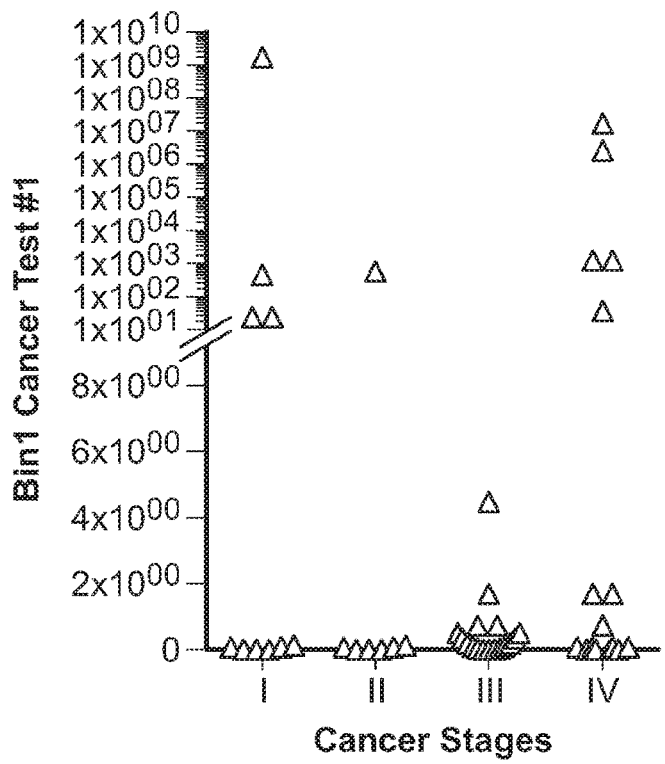
FIG. 8 is a plot showing 12a+/13− BIN1 levels from combined cancer samples as a function of cancer stage.
Figure 9A:
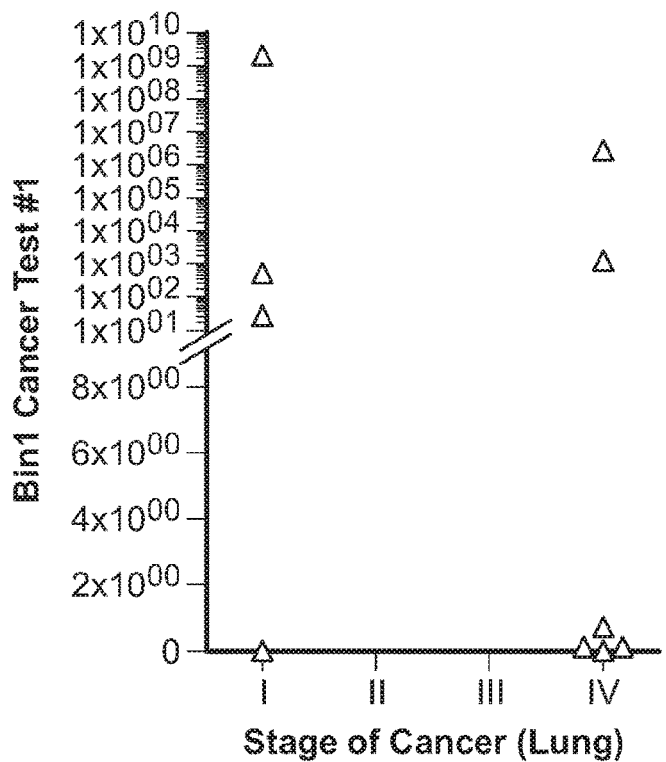
FIGS. 9A-9E are plots of 12a+/13− BIN1 levels from lung cancer (FIG. 9A), pancreatic cancer (FIG. 9B), colorectal (FIG. 9C), ovarian (FIG. 9D), and thyroid cancer (FIG. 9E) samples as a function of cancer stage.
Figure 9B:
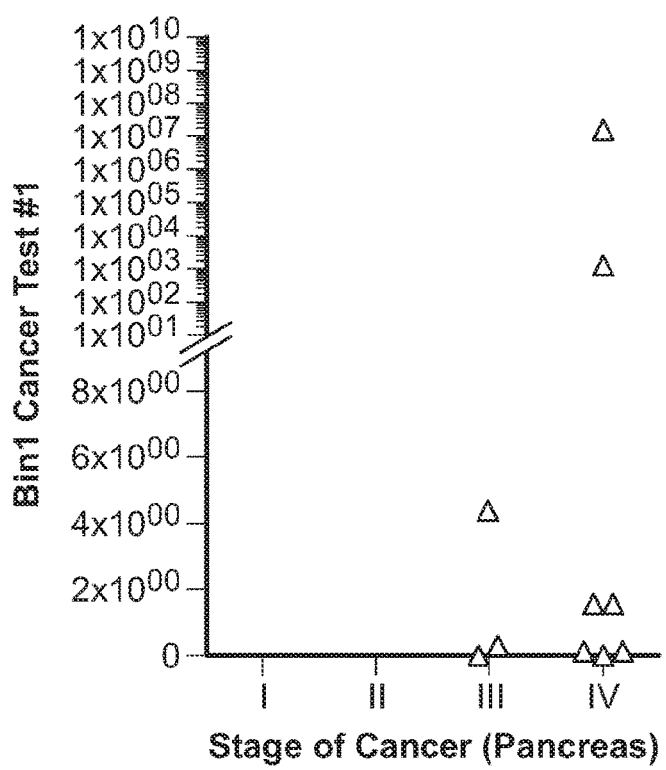
Figure 9C:
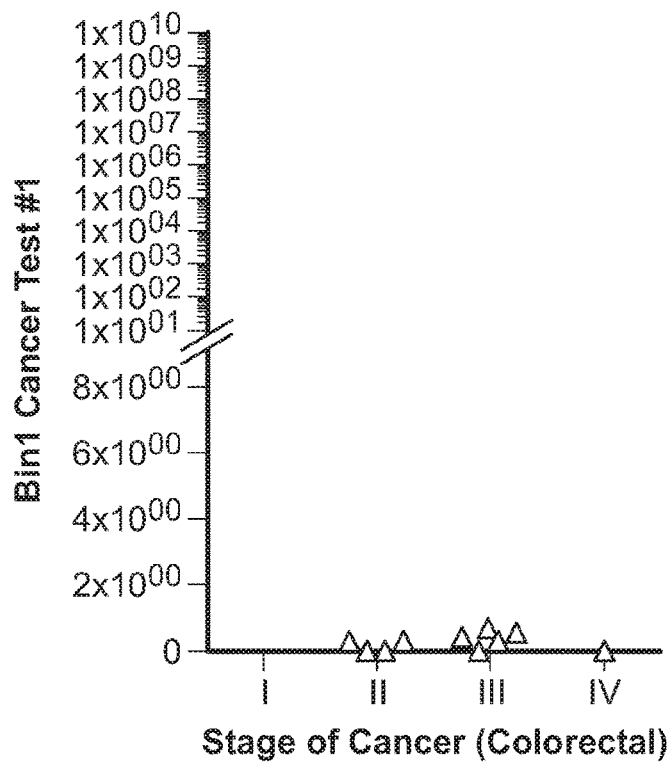
Figure 9D:
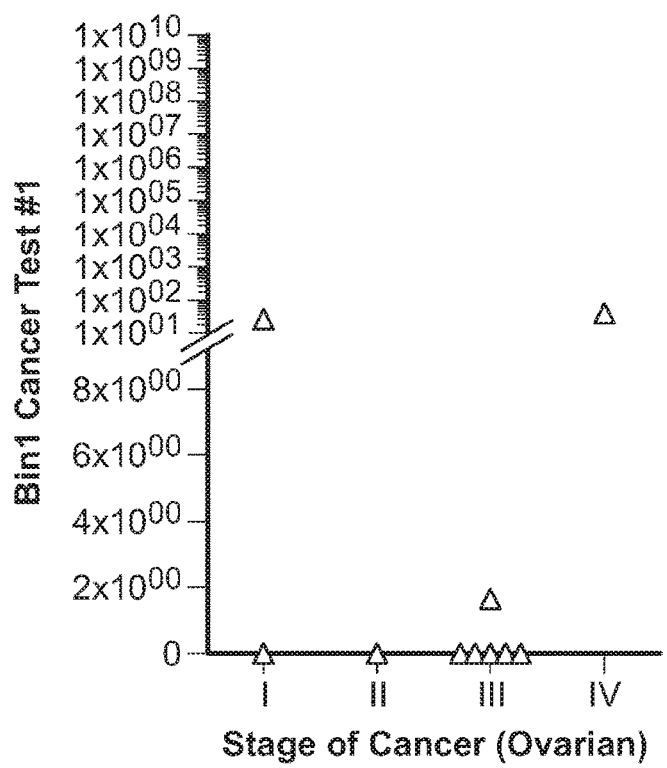
Figure 9E:
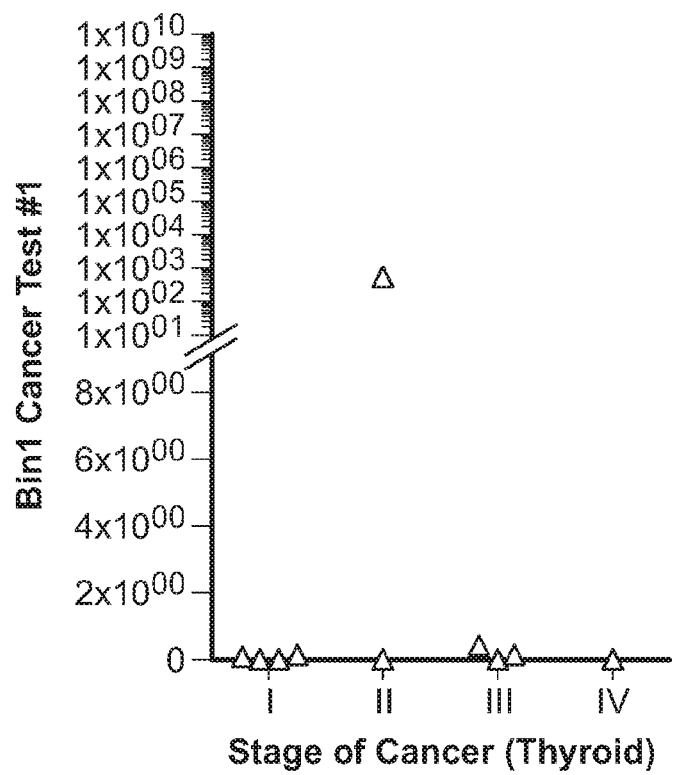

FIG. 8 represents the BIN1 Cancer Test #1 results in cancer patients related to the different stages of cancer progression (1 to IV) for all the cancer samples used in this study. An overall increase in BIN1 cancer test signal was observed in stage IV compared to stage III. FIGS. 9A-9E represent the test results related to the cancer stages, detected in each type of cancers. In lung cancer, two samples had high BIN1 cancer test results, one stage I and stage IV (FIG. 9A). In pancreas cancer, two stage IV cancer patients had relatively high Bin 1 cancer test results compared to the stage III cancer patients (FIG. 9B). In ovarian cancer, two samples had high Bin 1 cancer test results; one stage I and stage IV (FIG. 9C). Finally in thyroid cancer, the Bin 1 cancer test results were highest in a stage II cancer sample (FIG. 9E).

Thus, the BIN1 Cancer test detects a subset of cancer samples, in several cancers. These subsets may correspond to stage but do not necessarily correlate with stage. The BIN1 positive subsets may reflect tumor subtypes within these cancer diagnoses, i.e., subtypes that may have different biochemical pathways active or different host responses operating. This suggests that BIN1, by identifying subsets in lung, ovarian, thyroid, and pancreatic cancer, may be useful for treatment selection in these patients.

Example 4: BIN1 Detection in Blood Samples from Dogs Treated for Cancer

Materials and Methods

Dog Samples.

Fourteen blood samples from apparently healthy dogs (referred to as Normal) and forty three blood samples from dogs newly diagnosed with cancer (referred to as Cancer/Pre) were collected for this study. Several dogs underwent treatment, including surgical resection, and/or radiotherapy, and chemotherapy. A second blood sample was obtained from a subset of treated dogs one week and in some cases two weeks after treatment (Post1 and Post2, respectively).

Results

Figure 10:
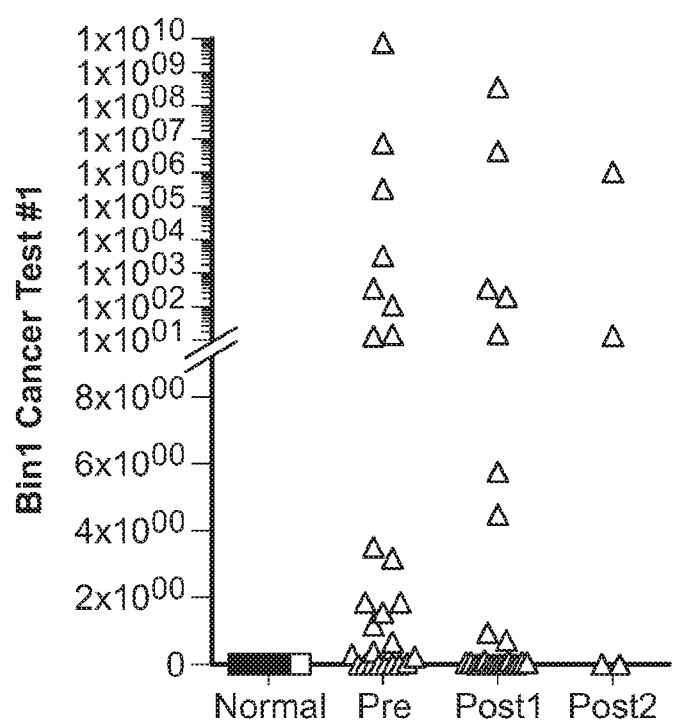
FIG. 10 is a plot showing 12a+/13− BIN1 levels in blood samples of normal and cancer dogs (pre- and post-treatments).

BIN1 Cancer Test #1 was used to analyze 57 dog samples (14 normals and 43 with new diagnosis) detect the levels of BIN1 cancer isoform in normal versus cancer dog samples, pre- and post-treatment. No detection of BIN1 cancer isoform was detected in normal samples (FIG. 10). Elevated BIN1 cancer isoform was detected in cancer samples. The levels of BIN1 cancer isoform decreased after cancer treatment (FIG. 10).

Figure 11A:
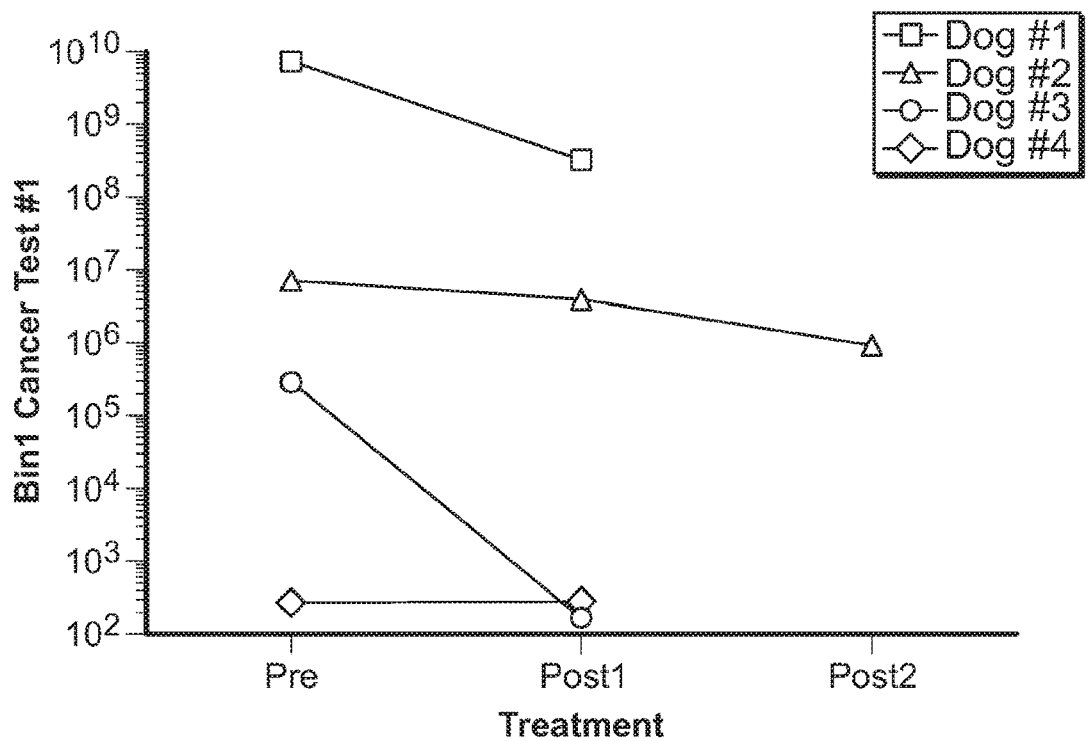
FIGS. 11A-11C are graphs of a time course showing 12a+/13− BIN1 levels in dogs.
Figure 11B:
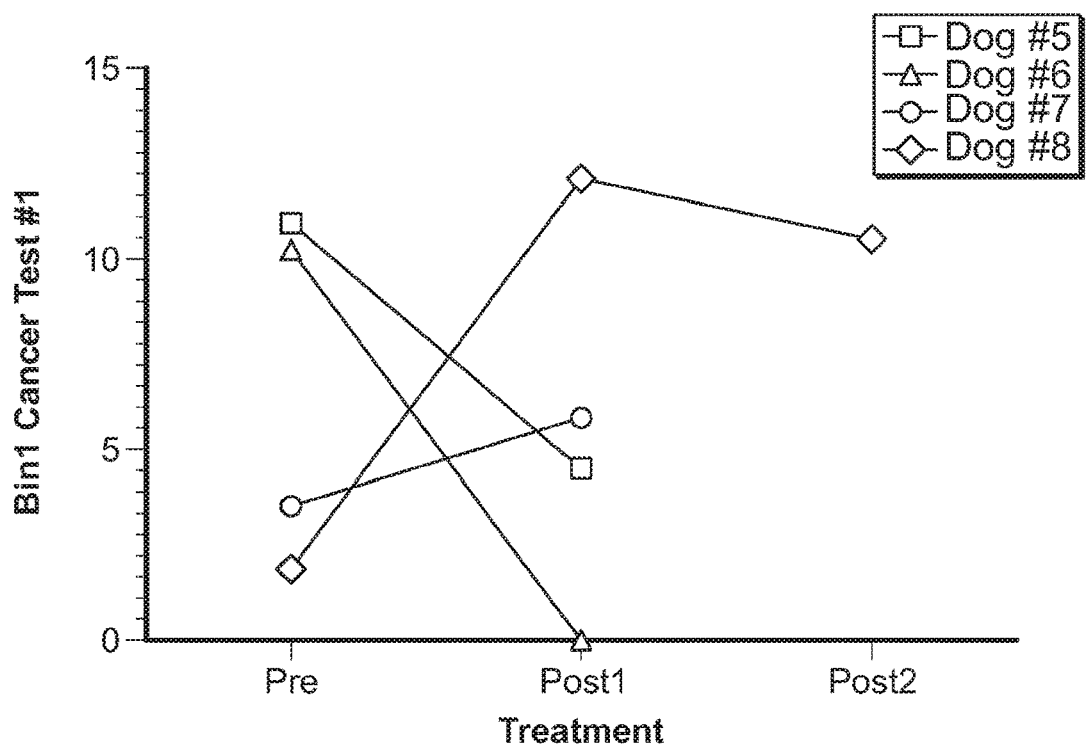
Figure 11C:
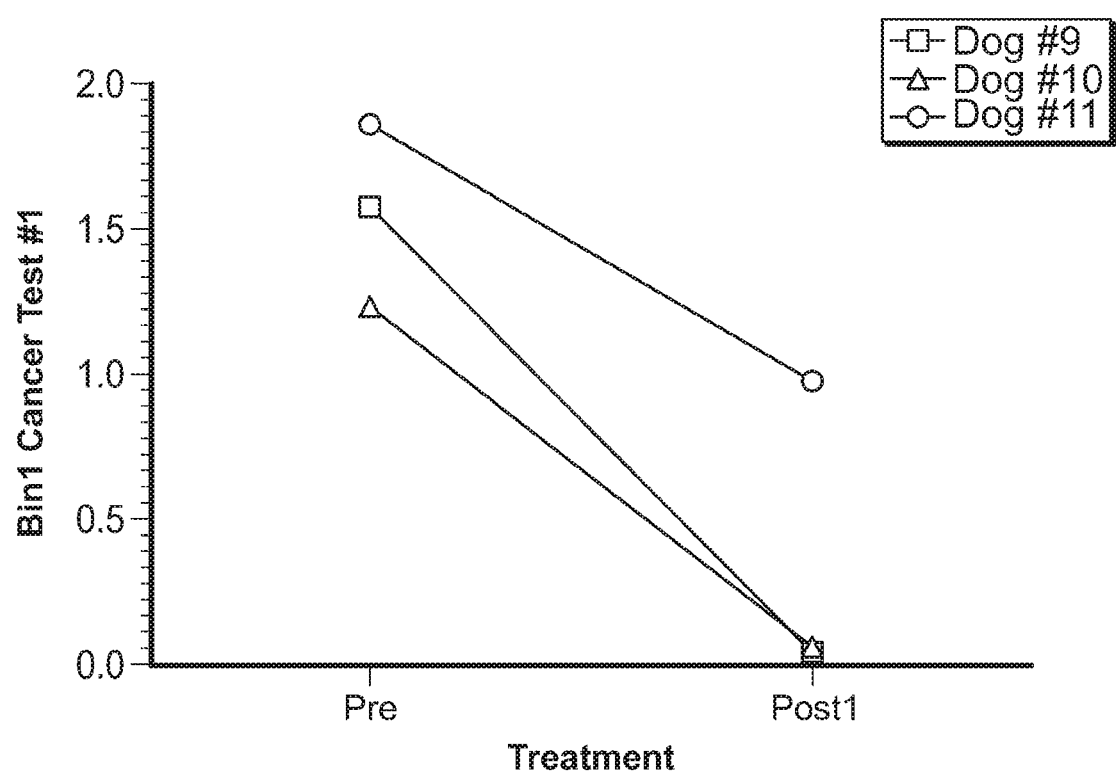

Fourteen pretreatment cancer samples showed elevated BIN1 cancer test results, with levels greater than 1, compared to normal (all normals were zero). Following cancer treatment, the level of BIN1 cancer isoform was decreased in eight out of eleven samples (FIGS. 11A-11C). No change in the level of BIN1 cancer isoform was observed in dog sample #4, #7, and #8 after treatment. Dog #4 had oral sarcoma with apparently clean 2 cm margins on surgical resection. However the high post-surgical BIN1 levels were suggestive of persistent disease, and the follow-up histopathology indicated that the margins were not clean and the cancerous cells had a high mitotic index. Treatment priority was shifted to palliative care and no further surgery was performed. Dog #7 presented with thyroid carcinoma that was surgically removed, but surgical and histopathology analysis showed vascular invasive metastasis, suggesting inadequate treatment. Dog #8 presented with a mast cell tumor that had poor response to therapy and the dog was later euthanized as the cancer continued to spread. Therefore, the high levels of BIN1 cancer isoform detected in blood samples correlated with cancer progression or with the absence of response to cancer treatment.

What is claimed is:

1. An antibody or antigen-binding fragment thereof which specifically binds to BIN1 comprising a heavy chain variable region (VH) and a light chain variable region (VL) wherein:
  (a) the VH comprises VH-CDR1, VH-CDR2, and VH-CDR3 amino acid sequences GFNIKDYY (SEQ ID NO: 10), IDPENGNT (SEQ ID NO: 11), and VRGEDYGGYAMDY (SEQ ID NO: 12), respectively; and
  (b) the VL comprises VL-CDR1, VL-CDR2, and VL-CDR3 amino acid sequences KSLLHSNGNTY (SEQ ID NO: 13), RMS (SEQ ID NO: 17), and MQHLEFPFT (SEQ ID NO:14), respectively.

2. The antibody or antigen-binding fragment of claim 1, wherein (a) the VH comprises the amino acid sequence of SEQ ID NO: 4; and (b) the VL comprises the amino acid sequence of SEQ ID NO: 6.

3. The antibody or antigen-binding fragment of claim 1, wherein the antibody is a monoclonal antibody, a humanized antibody, a chimeric antibody, a single chain antibody, or a recombinant antibody.

4. The antigen binding fragment of claim 1, wherein the antigen binding fragment is Fab, F(ab')2, or Fab'.

5. The antibody or antigen binding fragment of claim 1, wherein the antibody or antigen binding fragment binds to exon 12a of BIN1.

6. An antibody or antigen-binding fragment thereof which specifically binds to BIN1 comprising a heavy chain variable region (VH) and a light chain variable region (VL) wherein:
  (a) the VH comprises VH-CDR1, VH-CDR2, and VH-CDR3 amino acid sequences GFNIKDYY (SEQ ID NO: 10), IDPENGNT (SEQ ID NO: 11), and VRGEDYGGYAMDY (SEQ ID NO: 12), respectively; and
  (b) the VL comprises VL-CDR1, VL-CDR2, and VL-CDR3 amino acid sequences QDVSTA (SEQ ID NO: 15), WAS (SEQ ID NO: 18), and QQHYSTPFT (SEQ ID NO:16), respectively.

7. The antibody or antigen-binding fragment of claim 6, wherein (a) the VH comprises the amino acid sequence of SEQ ID NO: 4; and (b) the VL comprises the amino acid sequence of SEQ ID NO: 8.

8. The antibody or antigen-binding fragment of claim 6, wherein the antibody is a monoclonal antibody, a humanized antibody, a chimeric antibody, a single chain antibody, or a recombinant antibody.

9. The antigen binding fragment of claim 6, wherein the antigen binding fragment is Fab, F(ab')2, or Fab'.

10. The antibody or antigen binding fragment of claim 6, wherein the antibody or antigen binding fragment binds to exon 12a of BIN1.

11. A first recombinant nucleic acid encoding a heavy chain variable region (VH) of a BIN1 antibody or antigen binding fragment thereof and having the sequence of SEQ ID NO: 5, and a second recombinant nucleic acid encoding a light chain variable region (VL) of the BIN1 antibody or antigen binding fragment thereof and having the sequence selected from the group consisting of: SEQ ID NO: 7, and SEQ ID NO: 9.

12. A method for detecting 12a+ Bridging Integrator 1 (BIN1) expression levels in a blood sample comprising:
  contacting the blood sample with the antibody or antigen-binding fragment of claim 1; and
  detecting binding of the antibody or antigen-binding fragment to exon 12a of BIN1, optionally wherein the blood sample is whole blood, plasma, or serum.

13. A method for detecting 12a+ Bridging Integrator 1 (BIN1) expression levels in a blood sample comprising:
  (a) contacting the blood sample with the antibody or antigen-binding fragment of claim 6; and
  (b) detecting binding of the antibody or antigen-binding fragment to exon 12a of BIN1, optionally wherein the blood sample is whole blood, plasma, or serum.

* * * * *